(12) United States Patent
Kol et al.

(10) Patent No.: US 11,904,307 B2
(45) Date of Patent: *Feb. 20, 2024

(54) ORGANOMETALLIC COMPLEXES OF SEQUENTIAL TETRADENTATE MONOANIONIC LIGANDS AND USES THEREOF IN RING OPENING POLYMERIZATION OF CYCLIC ESTERS

(71) Applicant: Ramot at Tel-Aviv University Ltd., Tel-Aviv (IL)

(72) Inventors: Moshe Kol, Tel-Aviv (IL); Tomer Rosen, Tel-Aviv (IL); Yanay Popowski, Tel-Aviv (IL)

(73) Assignee: Ramot at Tel-Aviv University Ltd., Tel-Aviv (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/885,622

(22) Filed: Aug. 11, 2022

(65) Prior Publication Data

US 2022/0395820 A1 Dec. 15, 2022

Related U.S. Application Data

(62) Division of application No. 16/076,365, filed as application No. PCT/IL2017/050161 on Feb. 8, 2017, now Pat. No. 11,452,998.

(60) Provisional application No. 62/292,462, filed on Feb. 8, 2016.

(51) Int. Cl.
| | |
|---|---|
| B01J 31/00 | (2006.01) |
| B01J 31/22 | (2006.01) |
| C08G 63/82 | (2006.01) |
| C07D 401/14 | (2006.01) |
| C07D 213/36 | (2006.01) |

(52) U.S. Cl.
CPC ........ *B01J 31/2243* (2013.01); *C07D 213/36* (2013.01); *C07D 401/14* (2013.01); *C08G 63/823* (2013.01); *B01J 2231/54* (2013.01); *B01J 2531/004* (2013.01); *B01J 2531/0241* (2013.01); *B01J 2531/22* (2013.01); *B01J 2531/26* (2013.01)

(58) Field of Classification Search
None
See application file for complete search history.

(56) References Cited

U.S. PATENT DOCUMENTS

| | | | |
|---|---|---|---|
| 5,346,966 A | 9/1994 | Spinu | |
| 2011/0105695 A1 | 5/2011 | Schroeder | |
| 2017/0349710 A1 | 12/2017 | Jasinska-Walc | |
| 2018/0251593 A1 | 9/2018 | Kol et al. | |
| 2019/0039058 A1 | 2/2019 | Kol et al. | |
| 2021/0002417 A1 | 1/2021 | Kol et al. | |

FOREIGN PATENT DOCUMENTS

| | | |
|---|---|---|
| CN | 101970527 | 2/2011 |
| WO | WO 96/019519 | 6/1996 |
| WO | WO 2016/026859 | 2/2016 |
| WO | WO 2017/137990 | 8/2017 |
| WO | WO 2009/045881 | 9/2017 |
| WO | WO 2018/002941 | 1/2018 |

OTHER PUBLICATIONS

Notice of Allowance dated Jan. 24, 2023 from the US Patent and Trademark Office Re. U.S. Appl. No. 17/023,463. (29 pages).
US PTO Structure Search for U.S. Appl. No. 17/023,463 dated Jan. 3, 2023 (160 pages).
Advisory Action dated Apr. 13, 2021 From the US Patent and Trademark Office Re. U.S. Appl. No. 16/076,365. (7 Pages).
Communication Pursuant to Article 94(3) EPC dated Feb. 9, 2022 From the European Patent Office Re. Application No. 17/749,980/3. (6 Pages).
Communication Pursuant to Article 94(3) EPC dated Dec. 16, 2020 From the European Patent Office Re. Application No. 17819510..3. (4 Pages).
Communication Pursuant to Article 94(3) EPC dated Apr. 21, 2021 From the European Patent Office Re. Application No. 17749980.3. (6 Pages).
Communication Pursuant to Article 94(3) EPC dated Sep. 24, 2020 From the European Patent Office Re. Application No. 17749980.3. (5 Pages).
Communication Pursuant to Article 94(3) EPC dated Jan. 28, 2020 From the European Patent Office Re. Application No. 17749980.3. (3 Pages).
Final Official Action dated Jan. 7, 2021 from the US Patent and Trademark Office Rc. U.S. Appl. No. 16/076,365. (13 pages).
International Preliminary Report on Patentability dated Jan. 10, 2019 From the International Bureau of WIPO Re. Application No. PCT/IL2017/050735. (17 Pages).
International Search Report and the Written Opinion dated Sep. 3, 2017 From the International Searching Authority Re. Application No. PCT/IL2017/050735. (17 Pages).
International Search Report and the Written Opinion dated May 15, 2017 From the International Searching Authority Re. Application No. PCT/IL2017/050161. (10 Pages).
Notice of Allowance and Interview Summary dated May 17, 2022 From the US Patent and Trademark Office Re. U.S. Appl. No. 16/076,365. (20 Pages).
Notice of Allowance dated Jun. 17, 2020 from the US Patent and Trademark Office Re. U.S. Appl. No. 15/756,131. (11 pages).
Notification of Office Action dated Oct. 9, 2020 From the State Intellectual Property Office of the People's Republic of China Re. Application No. 201780003899.4. (4 Pages).

(Continued)

*Primary Examiner* — Yun Qian

(57) ABSTRACT

A new family of mononuclear organometallic complexes of a divalent metal bound to sequential tetradentate monoanionic {ONNN}-type ligands, and polymerization of cyclic esters such as lactides utilizing same are provided. Novel tetradentate monoanionic {ONNN}-type ligands usable for forming these complexes are also provided.

19 Claims, 5 Drawing Sheets

(56) References Cited

OTHER PUBLICATIONS

Figure 1:
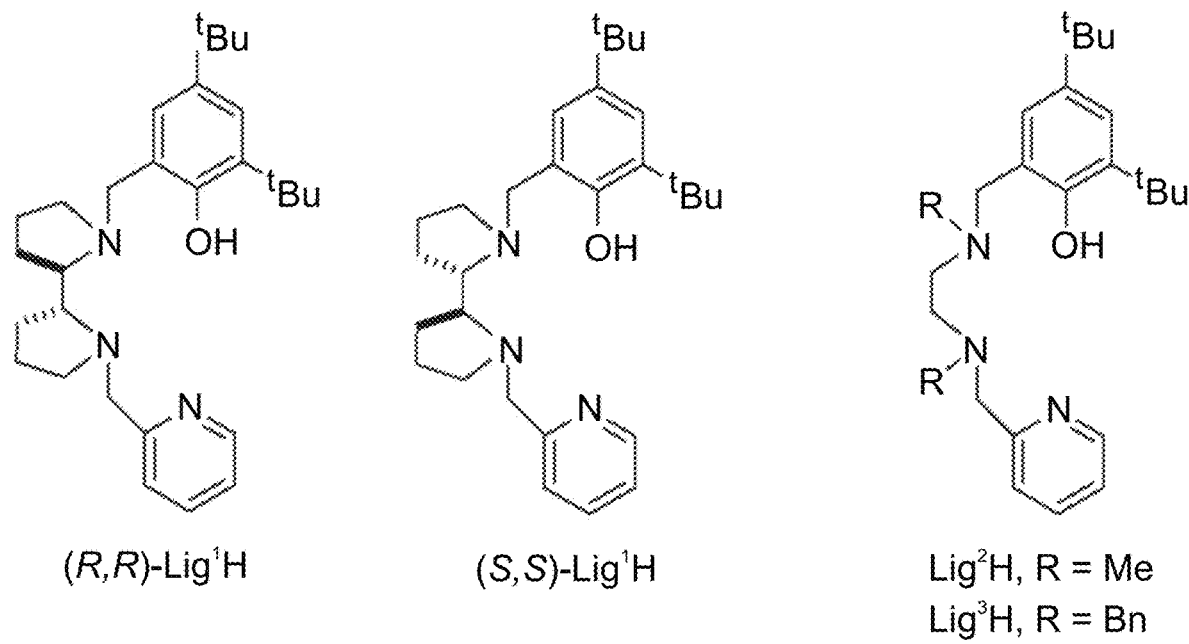
Figure 1:
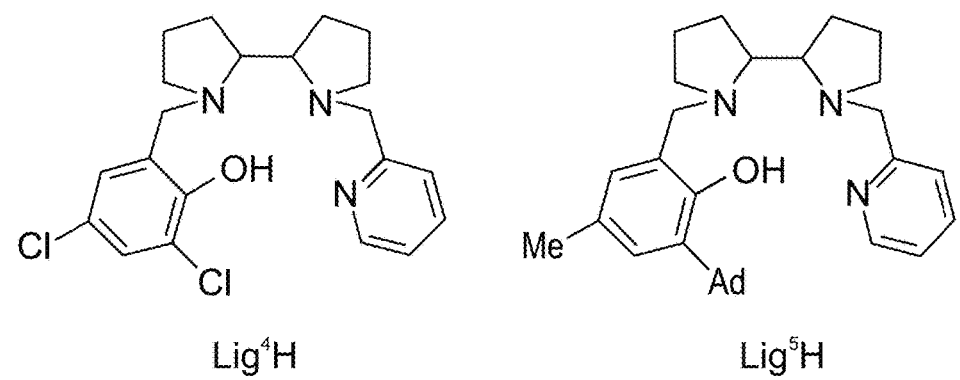
Figure 1:
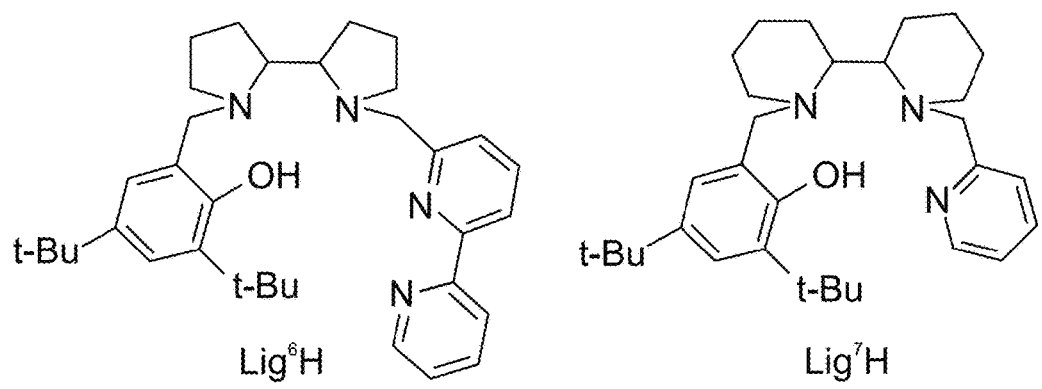

Notification of Office Action and Search Report dated Nov. 25, 2019 From the State Intellectual Property Office of the People's Republic of China Re. Application No. 201780003899.4 and Its Translation of Office Action Into English. (23 Pages).
Office Action dated Jul. 30, 2020 From the Israel Patent Office Re. Application No. 261023. (3 Pages).
Office Action dated Sep. 30, 2021 From the Israel Patent Office Re. Application No. 261023 and Its Translation Into English. (7 Pages).
Official Action dated Jun. 3, 2021 From the US Patent and Trademark Office Re. U.S. Appl. No. 16/076,365. (8 Pages).
Official Action dated Jul. 14, 2020 from the US Patent and Trademark Office Re. U.S. Appl. No. 16/076,365. (20 pages).
Official Action dated Dec. 22, 2021 from US Patent and Trademark Office Re. U.S. Appl. No. 16/076,365. (15 pages).
Official Action dated Jan. 29, 2020 From the US Patent and Trademark Office Re. Application No. 151756,131. (17 pages).
Restriction Official Action dated Apr. 17, 2020 from the US Patent and Trademark Office Re. U.S. Appl. No. 16/076,365. (7 pages).
Restriction Official Action dated Sep. 18, 2019 From the US Patent and Trademark Office Re. Application No. 15/756,131. (7 pages).
Supplementary European Search Report and the European Search Opinion dated Jan. 15, 2020 From the European Patent Office Re. Application No. 17819510.3. (9 Pages).
Supplementary European Search Report and the European Search Opinion dated May 22, 2019 From the European Patent Office Re. Application No. 17749980.3. (7 Pages).
Translation dated Oct. 30, 2020 of Notification of Office Action Dated Oct. 9, 2020 From the State Intellectual Property Office of the People's Republic of China Re. Application No. 201780003899.4. (3 Pages).
Anjos et al. "Synthesis, Characterization and Structure of a New Zinc(II) Complex Containing the Hexadentate N,N?,N,N ?- bis[(2-hydroxy-3,5-di-tert-butylbenzyl)(2-pyridylmethyl)]-ethylenediamine Ligand: Generation of Phenoxyl Radical Species", 358(11):3106-3114, Jul. 1, 2005.
Chen et al. "Magnesium and Zinc Complexes Containing Pendant Pyrazolylephenolate Ligands as Catalysts for Ring Opening Polymerization of Cyclic Esters", Journal of Organometallic Chemistry, 738: 1-9, Aug. 15, 2013.
Chiang et al. "Fe[III] Bipyrrolidine Phenoxide Complexes and Their Oxidized Analogues", Inorganic Chemistry, 53(11): 5810-5819, May 9, 2014.
Chomitz et al. "Synthesis and Reactivity of Metal Complexes Supported by the Tetradentate Monoanionic Ligand Bis(2-Picolyl)(2-Hydroxy-3,5-Di-Tert-Butylbenzyl)Amide (BPPA)", Inorganic Chemistry, XP055450351, 46(17): 7199-7209, Published on Web Jul. 26, 2007. p. 7201, Compound H(BPPA).
Contreras et al. "Synthesis of Epsilon-Caprolactone-B-L-Lactide Block Copolymers by Mean Sequential Polymerization, Using Diphenylzinc as Initiator", Polymer Bulletin, XP055450336, 71(7): 1661-1674, Published Online May 1, 2014.
Darensbourg et al. "Ring-Opening Polymerization of Lactides Catalyzed by Natural Amino-Acid Based Zinc Catalysts", Inorganic Chemistry, 49(5): 2360-2371, Feb. 1, 2010.
Dong et al. "Synthesis and Characterization of Stereoblock Poly(Lactic Acid)s", Engineering Plastics Applications, 39(11): 17-19, Dec. 2011 & English Translation.
Gross et al. "Zinc Complex Chemistry of N,N,O Ligands Providing A Hydrophobic Cavity", Inorganic Chemistry, XP055450349, 44(9): 3321-3329, Published on Web Apr. 5, 2005. p. 3322, Compounds L1, L2, L3, L4.
In't Veld ct al. "Melt Block Copolymerization of Epsilon-Caprolactone and L-Lactide", Journal of Polymer Science, Part A: Polymer Chemistry, XP055450333, 35(2): 219-226, Jan. 30, 1997.
Labourdette et al. "Unusually Stable Chiral Ethyl Zinc Complexes: Reactivity and Polymerization of Lactide", Organometallics, 28(5): 1309-1319, Publication on Web Feb. 11, 2009.
Leavell et al. "Conformational Studies of ZN-Ligand-Hexose Diastereomers Using Ion Mobility Measurements and Density Functional Theory Calculations", Journal of the American Society of Mass Spectrometry, 13(3): 284-293, Published Online Jan. 22, 2002. p. 288, Fig.3.
Luo et al. "Monoprotic Tetradentate N3O-Donor Ligands and Their Cu(II) and Ni(II) Complexes", Inorganic Chemistry, 38(9): 2071-2078, Apr. 17, 1999. p. 2071, Chart 1, p. 2076, Fig.1.
Michel et al. "Galactose Oxidase Models: Creation and Modification of Proton Transfer Coupled to Copper(II) Coordination Processes in Pro-Phenoxyl Ligands", European Journal of Inorganic Chemistry, XP055450366, 2006(18): 3684-3696, Published Online Aug. 3, 2006. p. 3685, Scheme 1, Compounds HL-tBu, HLH, HLMe.
Michel et al. "Galactose Oxidase Models: Solution Chemistry, and Phenoxyl Radical Generation Mediated by the Copper Status", Chemistry—A European Journal, XP055450364, 10(17): 4115-4125, Jul. 21, 2004. p. 4117, Fig. 1b, Compounds HLOMe, HLtBu,HLF, Fig.1c, Compound HLotBu.
Nagataki et al. "Ligand Effects on NiII-Catalysed Alkane-Hydroxylation With M-CPBA", Dalton Transactions, XP055450360, 2007(11): 1120-1128, Published Online Feb. 6, 2007. p. 1121, Compounds DtbpPym2H, DtbpPye2H.
Rosen et al. "Divergent [{ONNN}Mg—Cl] Complexes in Highly Active and Living Lactide Polymerization", Chemical Science, XP055450370, 8: 5476-5481, May 26, 2017.
Rosen et al. "Tailor-Made Stereoblock Copolymers of Poly(Lactic Acid) by a Truly Living Polymerization Catalyst", Journal of the American Chemical Society, Jacs, XP055587944, 138: 12041-12044, Sep. 7, 2016.
Rosen et al. "Zinc Complexes of Sequential Tetradentate Monoanionic Ligands in the Isoselective Polymerization of Rac-Lactide", Chemistry—A European Journal, XP055450367, 22(33): 11533-11536, Jul. 4, 2016. Gable 1, Layout 2, 2nd Scheme.
Rosen et al. Divergent [{ONNN}Mg—Cl] Complexes in Highly Active and Living Lactide Polymerization, Chemical Science, 8: 5476-5481, Published Online May 26, 2017.
Schneiderman et al. "Poly(Lactide)-Block-Poly(Epsilon-Caprolactone-Co-Epsilon-Decalactone)-Block-Poly(Lactide) Copolymer Elastomers", Polymer Chemistry, XP055450337, 6(19): 3641-3651, May 21, 2015.
Shimazaki et al. "Zinc(II)-Phenoxyl Radical Complexes: Dependence on Complexation Properties of Zn-Phenolate Species", Inorganica Chimica Acta, XP026020367, 362(7): 2467-2474, Available Online Nov. 18, 2008. Fig.1, Compounds tBul, tBul(Mepy), tBul(Mepy)2.
Stridsberg "Controlled Ring-Opening Polymerization: Polymers With Designed Macromolecular Architecture", PhD Dissertation, Department of Polymer Technology, Royal Institute of Technology, Stockholm, Sweden, XP055450329, p. 1-94, Mar. 3, 2000. Para 5.5.
Wang ct al. "[ONN]-Type Amine Pyridinc(s) Phenolate-Based Oxovanadium(v) Catalysts for Ethylene Homo-and Copolymerization", Dalton Transactions, XP055450340, 43(34): 12926-12934, Jul. 31, 2014. p. 12927, Compound 2a.
Wang et al. "Highly Active Magnesium Initiators for Ring-Opening Polymerization of Rac-Lactide", Macromolecules, XP055450372, 43(16): 6535-6537, Published on Web Jul. 27, 2010.
Wei et al. "Synthesis of Poly(Epsilon-Caprolactone)-Poly(L-Lactide) Block Copolymers by Melt or Solution Sequential Copolymerization Using Nontoxic Dibutylmagnesium as Initiator", Polymer Bulletin, XP019655258, 61(4): 407-413, Published Online Jul. 4, 2008.
Williams et al. "A Highly Active Zinc Catalyst for the Controlled Polymerization of Lactide", Journal of the American Chemical Society, JACS, 125(37): 11350-11359, Sep. 17, 2003.
Wong et al. "Mononuclear Iron(III) Complexes Supported by Tripodal N3O Ligands: Synthesis, Structure and Reactivity Towards DNA Cleavage", Inorganica Chimica Acta, XP026977168, 363(6): 1246-1253, Available Online Dec. 29, 2009. Fig.1, Compound of General Formula III (Each of R1 and R2 Is T-But and R3 Is H or Me), Scheme 1, Compounds HL1, HL2, HL3.
Zhang et al. "Versatile Supramolecular Copper(II) Complexes for Henry and Aza-Henry Reactions", Advanced Synthesis & Catalysis, XP055732198, 351(9): 1255-1262, Published Online Jun. 2, 2009.
Zheng et al. "Zinc and Enolato-Magnesium Complexes Based on Bi-, Tri- and Tetradentate Aminophenolate Ligands", New Journal of Chemistry, XP009123110, 32(12): 2279-2291, Published Online Oct. 14, 2008.

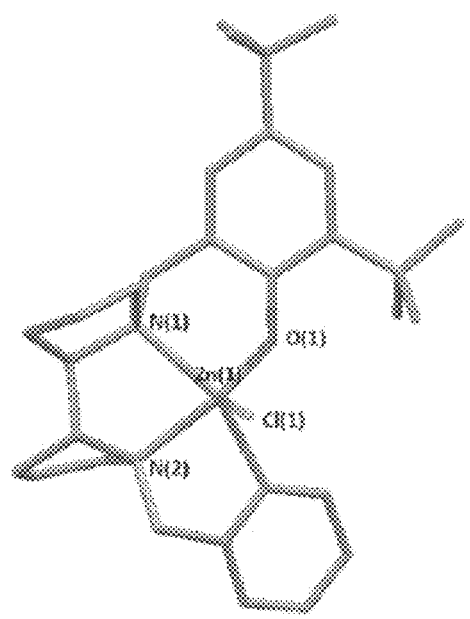
FIG. 2A
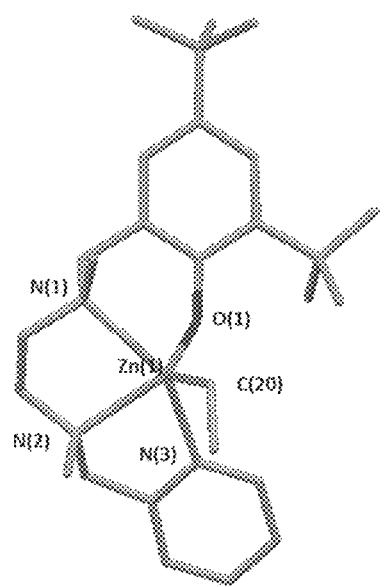
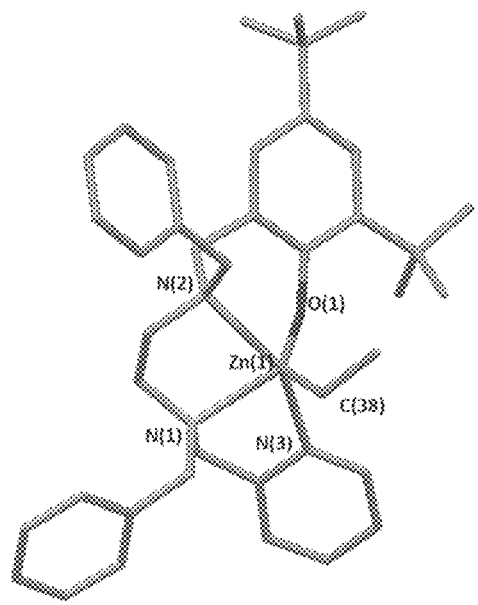
FIG. 2B
FIG. 2C

ORGANOMETALLIC COMPLEXES OF SEQUENTIAL TETRADENTATE MONOANIONIC LIGANDS AND USES THEREOF IN RING OPENING POLYMERIZATION OF CYCLIC ESTERS

RELATED APPLICATIONS

This application is a division of U.S. patent application Ser. No. 16/076,365, filed on Aug. 8, 2018, which is a National Phase of PCT Patent Application No. PCT/IL2017/050161 having International Filing Date of Feb. 8, 2017, which claims the benefit of priority under 35 USC § 119(e) of U.S. Provisional Patent Application No. 62/292,462 filed on Feb. 8, 2016. The contents of the above applications are all incorporated by reference as if fully set forth herein in their entirety.

FIELD AND BACKGROUND OF THE INVENTION

The present invention, in some embodiments thereof, relates to chemistry and, more particularly, but not exclusively, to novel organometallic complexes, and to uses thereof in catalytic ring opening polymerization of cyclic esters.

Biodegradable materials derived from bio-renewable resources are attracting considerable current interest as possible alternatives to the commonly employed plastics such as polypropylene that are derived from depleting petroleum feedstock. Aliphatic polyesters such as poly(lactic acid) (PLA), and poly(ε-caprolactone) (PCL) have been explored and introduced towards this end. Of these, the most commercially promising material is PLA due to its mechanical and physical properties and its synthesis from starting materials originating from biomass such as corn. As the degradation products of PLA are non-toxic, it has found biomedical application as well as commodity applications.

The most practical method for the production of these polyesters is the catalytic Ring Opening Polymerization (ROP) of cyclic esters (lactones). Lactide is chiral, having two stereogenic centers leading to three possible stereoisomers: L-lactide (the natural stereoisomer), D-lactide, and meso-lactide.

Ring opening polymerization of lactides may therefore lead to PLAs of various tacticities, (e.g., heterotactic, isotactic (racemic and stereoblock), and syndiotactic), as shown in Scheme 1 below. While heterotactic PLA is amorphous, isotactic PLA derived from rac-LA tends to crystallize as a stereocomplex whose physical properties are superior to those of homochiral isotactic PLA.

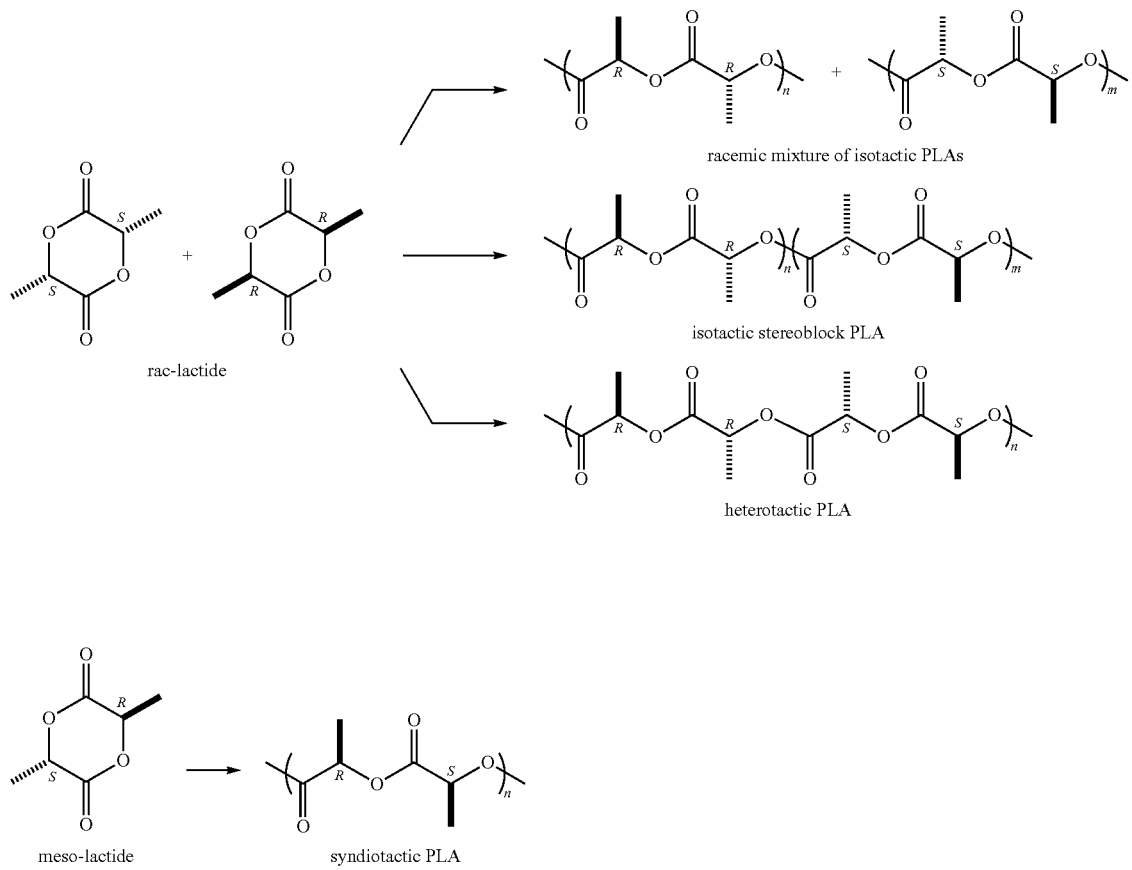

Scheme 1

Ring opening polymerization (ROP) of lactides mediated by metal-based catalysts typically follows the coordination-insertion mechanism of a lactide ester bond to a metal-alkoxo bond, as shown in Scheme 2.

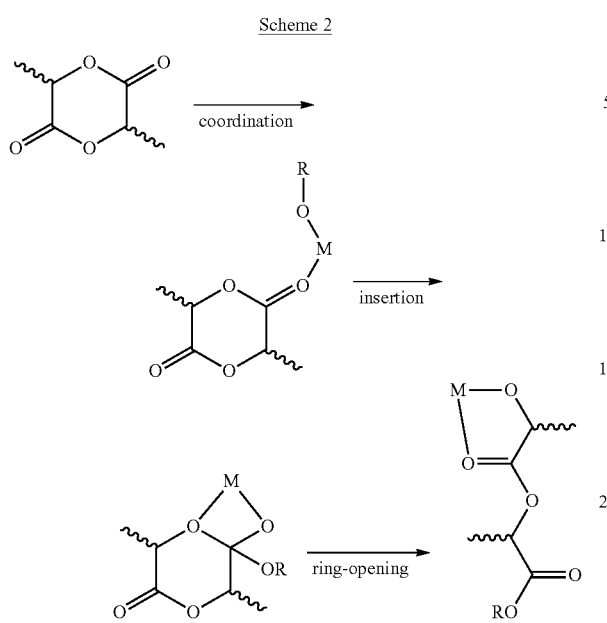

Scheme 2

For rac-LA polymerization, the stereochemical preference could be either heterochiral (leading to heterotactic PLA) or homochiral (leading to one of the forms of isotactic PLA).

The industrial process for L-lactide polymerization takes place at high temperatures in the melt and employs tin(II) octoate as catalyst. More advanced PLA generations are expected to include different types of lactide isomers assembled in an ordered (regioregular) fashion.

Tin octoate has two disadvantages: (1) possible toxicity of tin traces remaining in the polymer; and (2) inability to differentiate between the stereoisomers of lactide which leads to stereo-irregular amorphous plastic when the monomer starting material is changed from L-lactide to isomer mixture of lactides.

Therefore, in the past 15 years, there has been an enormous effort to try and develop more advanced catalysts. The requirements of such catalysts are: high activities and turnover numbers leading to high molecular weight-polymers; control of stereoregularity of the polymer with emphasis on isospecific polymerization of racemic-lactide; low cost and low toxicity.

The most successful catalysts for lactide and related cyclic-ester polymerizations are metal complexes featuring a chelating ligand that remains bound to the metal, and a labile alkoxo group that initiates the polymerization process. Many catalysts that answer part of these requirements have been described, however, catalysts that address all demands, namely: high activity, high polymer stereoregularity and molecular weight, and non-toxicity, are still sought for.

Catalysts for lactide ring opening polymerization in which zinc is embedded in various ligand environments are described for example, in Wheaton et al. Dalton Trans. 2009, 4832-4846; Chisholm et al. J. Am. Chem. Soc. 2000, 122, 11845-11854; Chamberlain et al. J. Am. Chem. Soc. 2001, 123, 3229-3238; Chen et al. Macromolecules 2006, 39, 3745-3752; Darensbourg et al. Inorg. Chem. 2010, 49, 2360-2371; and Yu et al. Organometallics, 2013, 32, 3262-3268. While a few of these catalysts exhibit high activities, they traditionally tend to be either non-stereoselective or hetero selective.

Isoselective polymerization of rac-LA has been reported, for example, by Wang and Ma, Chem. Commun. 2013, 49, 8686-8688; Wang et al. Macromolecules 2014, 47, 7750-7764; Abbina and Du, ACS Macro. Lett. 2014, 3, 689-692; Mou et al. Chem. Commun. 2014, 50, 11411-11414; Honrado et al. Organometallics, 2015, 34, 3196-3208.

A zinc catalyst obtainable using a pre-catalyst featuring an ethylzinc bound to a tridentate monoanionic diamine-monophenolate {ONN} ligand, the structure of which is presented below, was shown to exhibit very high activity in lactide ROP, upon addition of ethyl alcohol, consuming 500 equivalents of rac-LA in 5 minutes at room temperature [Williams et al. J. Am. Chem. Soc. 2003, 125, 11350-11359]. However, the PLA obtained using this catalyst was atactic. This catalyst was found to be dinuclear in the solid state and mononuclear in solution.

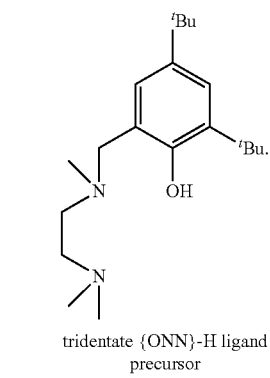 [SMILES: CN(C)CCN(C)Cc1cc(C(C)(C)C)cc(C(C)(C)C)c1O]

tridentate {ONN}-H ligand precursor

A later attempt to induce stereoselectivity by employing a chiral diaminocyclohexane-based ligand led to a robust zinc complex, whose ethyl group could not be readily replaced with an active alkoxo group [Labourdette et al. Organometallics, 2009, 28, 1309-1319].

Recently, a tetradentate monoanionic ligand featuring a chiral bipyrrolidine core and phenolate and pyridine peripheral donors was described in the context of iron electrochemistry [Chiang et al. Inorg. Chem. 2014, 53, 5810-5819].

Additional background art includes Rosen et al., Chem. Eur. J. 2016, 22, 11533-11536; and Rosen et al., J. Am. Chem. Soc. 2016, 138, 12041-12044.

SUMMARY OF THE INVENTION

As controlling the tacticity of poly(lactic acid) (PLA) obtained by ring opening polymerization (ROP) of lactide (or any other cyclic ester with a chiral center) is highly desirable, isoselective ROP catalysts are extensively sought for. However, to date, organometallic catalysts which feature both high reactivity and stereochemical control in ROP of lactides have not been uncovered.

The present inventors have now designed and successfully practiced a new family of mononuclear organometallic complexes comprising sequential tetradentate monoanionic {ONNN}-type ligands.

The present inventors have practiced exemplary such complexes, based on Zn-Et, as pre-catalysts, and have demonstrated that exchanging of the ethyl group of these catalysts with a benzyloxy group of a co-catalyst is accomplished fast, without any signs of complex decomposition. The benzyloxy complexes show catalytic activity in ring opening polymerization (ROP) of racemic lactide ranging from high to very high. Living or immortal polymerization is attained by varying the added ratio of benzyl alcohol. A clear tendency to isoselective polymerization is observed, reaching $P_m$ higher than 80%.

The present inventors have further practiced complexes based on Mg—Cl and Mg-HDMS, and have demonstrated that such complexes are even more reactive, leading to highly isoselective polymerization within about 1 minute.

Embodiments of the present invention therefore relate to novel complexes comprising a sequential tetradentate (optionally pentadentate or higher) monoanionic {ONNN}-type ligand, represented by Formula I herein, to uses thereof in ring opening polymerization of cyclic esters such as lactides, to polymers (e.g., strereoselective polymers) obtainable by these processes, to articles-of-manufacturing containing such polyesters, to novel sequential tetradentate (optionally pentadentate or higher) monoanionic {ONNN}-type ligands usable in preparing such complexes, and to processes of preparing the ligands and complexes.

According to an aspect of some embodiments of the present invention there is provided an organometallic complex represented by Formula I:

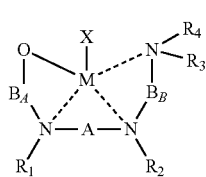

Formula I wherein:
the dashed line represents a coordinative bond;
M is a divalent metal;
X is a monoanionic ligand;
A, $B_A$ and $B_B$ are each independently a bridging moiety of 1 to 12 carbon atoms;
$R_1$ and $R_2$ are each independently hydrogen, alkyl, cycloalkyl, aryl or alternatively, one or both of $R_1$ and $R_2$ form together, optionally with one or more carbon atoms in A, a heteroalicyclic or heteroaromatic, 5-membered, 6-membered or 7-membered ring; and
$R_3$ and $R_4$ are each independently hydrogen, alkyl, cycloalkyl, aryl or alternatively, one or both of $R_3$ and $R_4$ form together with one or more carbon atoms in $B_B$, a heteroalicyclic or heteroaromatic, 5-membered, 6-membered or 7-membered ring.

According to some of any of the embodiments described herein, M is selected from zinc, magnesium, and calcium.

According to some of any of the embodiments described herein, M is zinc.

According to some of any of the embodiments described herein, M is magnesium.

According to some of any of the embodiments described herein, X is selected from alkyl, cycloalkyl, aryl, amide, alkoxy, thioalkoxy, aryloxy, thioalryloxy, halo and amine (e.g., a substituted amine, as described herein).

According to some of any of the embodiments described herein, X is alkyl.

According to some of any of the embodiments described herein, X is halo.

According to some of any of the embodiments described herein, X is amine substituted by at least one silyl group.

According to some of any of the embodiments described herein, the $B_A$ bridging moiety has a general Formula:

wherein:
m is an integer of from 1 to 6, or from 1 to 4, or from 1 to 2;
Ra and Rb are each independently hydrogen, alkyl, cycloalkyl, aryl, heteroaryl, heteroalicyclic, hydroxyl, alkoxy, thiol, thioalkoxy, aryloxy, and amine, wherein when m is other than 1, Ra and Rb in each (CRaRb) unit can be the same or different, and one or both Ra and Rb in one unit can form a 5-membered, 6-membered or 7-membered alicyclic, heteroalicyclic, aromatic or heteroaromatic ring with one or both Ra and Rb of an adjacent unit; and
$R_{17}$-$R_{20}$ are each independently hydrogen, alkyl, cycloalkyl, aryl, heteroaryl, heteroalicyclic, hydroxyl, alkoxy, thiol, thioalkoxy, aryloxy, and amine, or, alternatively, two or more of $R_{17}$-$R_{20}$ form together a 5-membered, 6-membered or 7-membered alicyclic, heteroalicyclic, aromatic or heteroaromatic ring.

According to some of any of the embodiments described herein, m is 1.

According to some of any of the embodiments described herein, Ra and Rb are each hydrogen.

According to some of any of the embodiments described herein, $R_{17}$-$R_{20}$ form together a substituted or unsubstituted aromatic ring.

According to some of any of the embodiments described herein, the $B_B$ bridging moiety has a general Formula:

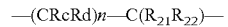

wherein:
n is an integer of from 1 to 6, or from 1 to 4, or from 1 to 2;
Rc and Rd are each independently hydrogen, alkyl, cycloalkyl, aryl, heteroaryl, heteroalicyclic, hydroxyl, alkoxy, thiol, thioalkoxy, aryloxy, and amine, wherein when n is other than 1, Rc and Rd in each (CRcRd) unit can be the same or different, and one or both Rc and Rd in one unit can form a 5-membered, 6-membered or 7-membered alicyclic, heteroalicyclic, aromatic or heteroaromatic ring with one or both Rc and Rd of an adjacent unit; and
$R_{21}$ and $R_{22}$ are each independently hydrogen, alkyl, cycloalkyl, aryl, heteroaryl, heteroalicyclic, hydroxyl, alkoxy, thiol, thioalkoxy, aryloxy, and amine, or, alternatively, at least two of $R_3$, $R_4$, $R_{21}$ and $R_{22}$ form together a 5-membered, 6-membered or 7-membered heteroalicyclic or heteroaromatic ring.

According to some of any of the embodiments described herein, n is 1.

According to some of any of the embodiments described herein, Rc and Rd are each hydrogen.

According to some of any of the embodiments described herein, $R_3$, $R_4$, $R_{21}$ and $R_{22}$ form together a substituted or unsubstituted heteroaromatic ring.

According to some of any of the embodiments described herein, the complex is represented by Formula IA:

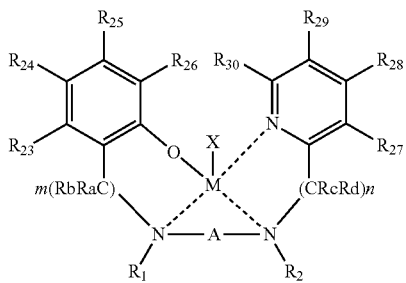

Formula IA wherein:

$R_{23}$-$R_{30}$ are each independently selected from the group consisting of hydrogen, alkyl, cycloalkyl, aryl, halo, alkoxy, aryloxy, trialkylsilyl, heteroalicyclic, heteroaryl and amine.

According to some of any of the embodiments described herein, at least one of $R_{23}$-$R_{26}$ is alkyl.

According to some of any of the embodiments described herein, at least one of $R_{24}$ and $R_{26}$ is alkyl.

According to some of any of the embodiments described herein, at least one of $R_{23}$-$R_{26}$ is halo.

According to some of any of the embodiments described herein, at least one of $R_{23}$-$R_{26}$ is a bulky rigid group.

According to some of any of the embodiments described herein, each of $R_{27}$-$R_{30}$ is hydrogen.

According to some of any of the embodiments described herein, at least one of $R_{27}$-$R_{30}$ is a heteroalicyclic or a heteroaryl.

According to some of any of the embodiments described herein, the A bridging moiety has a general Formula A1, A2 or A3:

—$C_1R_5R_6$—   Formula A1

—$C_1(R_7R_8)$—$C_2(R_9R_{10})$—   Formula A2

—$C_1(R_{11}R_{12})$—$C_2(R_{13}R_{14})$—$C_3(R_{15}R_{16})$—   Formula A3 wherein $R_5$-$R_{12}$, $R_{15}$ and $R_{16}$ are each independently selected from the group consisting of hydrogen, alkyl, cycloalkyl, aryl, heteroaryl and heteroalicyclic, $R_{13}$ and $R_{14}$ are each independently selected from the group consisting of hydrogen, alkyl, cycloalkyl, aryl, heteroaryl, heteroalicyclic, hydroxyl, alkoxy, thiol, thioalkoxy, aryloxy, and amine or, alternatively, at least two of $R_1$, $R_2$ and $R_5$-$R_6$ in Formula A1, or at least two of $R_1$, $R_2$ and $R_7$-$R_{10}$ in Formula A2 or at least two of $R_1$, $R_2$ and $R_{11}$-$R_{16}$ in Formula A3 form a 5 to 7-membered alicyclic, heteroalicyclic, aromatic or heterocyclic ring.

According to some of any of the embodiments described herein, the A bridging moiety has the Formula A2.

According to some of any of the embodiments described herein, each of $R_7$-$R_{10}$ is hydrogen.

According to some of any of the embodiments described herein, $R_7$ and $R_1$ form the heteroalicyclic ring.

According to some of any of the embodiments described herein, $R_9$ and $R_2$ form the heteroalicyclic ring.

According to some of any of the embodiments described herein, at least one, or both, of $R_1$ and $R_2$ is alkyl.

According to an aspect of some embodiments of the present invention there is provided a process of ring opening polymerization of a cyclic ester, the process comprising contacting the cyclic ester with a catalyst system comprising an organometallic complex according as described herein in any of the respective embodiments and combination thereof.

According to some of any of the embodiments described herein, the catalyst system further comprises a co-catalyst.

According to some of any of the embodiments described herein, the co-catalyst is Rk-OH, wherein Rk is alkyl, cycloalkyl, alkaryl or aryl.

According to some of any of the embodiments described herein, the cyclic ester is a lactide.

According to some of any of the embodiments described herein, the cyclic ester is a lactone.

According to an aspect of some embodiments of the present invention there is provided polyester obtainable by the process as described herein in any of the respective embodiments and any combination thereof.

According to some of any of the embodiments described herein, the polyester is characterized by a polydispersity (Mw/Mn) lower than 1.5, or lower than 1.2.

According to some of any of the embodiments described herein, the polyester is characterized by Pm of at least 0.6, or at least 0.7.

According to an aspect of some embodiments of the present invention there is provided ligand precursor compound represented by Formula II:

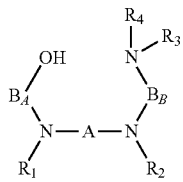

Formula II wherein:

A, $B_A$ and $B_B$ are each independently a bridging moiety of 1 to 12 carbon atoms;

$R_1$ and $R_2$ are each independently hydrogen, alkyl, cycloalkyl, aryl or alternatively, one or both of $R_1$ and $R_2$ form together, optionally with one or more carbon atoms in A, a heteroalicyclic or heteroaromatic, 5-membered, 6-membered or 7-membered ring; and $R_3$ and $R_4$ are each independently hydrogen, alkyl, cycloalkyl, aryl or alternatively, one or both of $R_3$ and $R_4$ form together with one or more carbon atoms in $B_B$, a heteroalicyclic or heteroaromatic, 5-membered, 6-membered or 7-membered ring.

According to some of any of the embodiments described herein for a ligand precursor compound: when $R_3$ and $R_4$ from together with $B_B$ an unsubstituted 6-membered heteroatomic ring, $B_A$ is other than benzyl; or when $R_3$ and $R_4$ from together with $B_B$ an unsubstituted 6-membered heteroatomic ring and/or $B_A$ is benzyl, A is a bridging moiety of 1 or of 3 to 12 carbon atoms; or when $R_3$ and $R_4$ from together with $B_B$ an unsubstituted 6-membered heteroatomic ring and/or $B_A$ is benzyl, at least one of $R_1$ and $R_2$ do not form together with carbon atoms in A a heteroalicyclic 5-membered ring; or when $R_3$ and $R_4$ from together with $B_B$ an unsubstituted 6-membered heteroatomic ring; each of $R_1$ and $R_2$ form together with carbon atoms in A a heteroalicyclic 5-membered ring; and $B_A$ is benzyl, the benzyl is substituted by at least one halo and/or at least one bulky rigid group; or when $B_A$ is benzyl; and each of $R_1$ and $R_2$ form together with carbon atoms in A a heteroalicyclic 5-membered ring; and $R_3$ and $R_4$ from together with $B_B$ a 6-membered heteroatomic ring, the heteroaromatic ring is substituted.

According to some of any of the embodiments described herein, the ligand precursor compound is represented by Formula IIA:

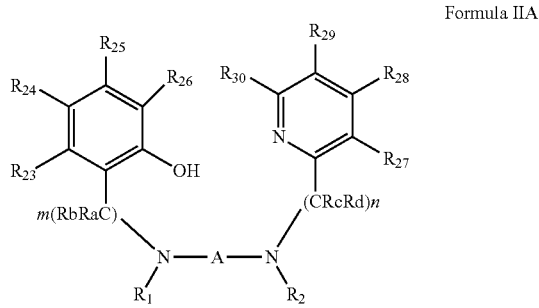

Formula IIA wherein:

Ra and Rb are each independently hydrogen, alkyl, cycloalkyl, aryl, heteroaryl, heteroalicyclic, hydroxyl, alkoxy, thiol, thioalkoxy, aryloxy, and amine, wherein when m is other than 1, Ra and Rb in each (CRaRb) unit can be the same or different, and one or both Ra and Rb in one unit can form a 5-membered, 6-membered or 7-membered alicyclic, heteroalicyclic, aromatic or heteroaromatic ring with one or both Ra and Rb of an adjacent unit;

Rc and Rd are each independently hydrogen, alkyl, cycloalkyl, aryl, heteroaryl, heteroalicyclic, hydroxyl, alkoxy, thiol, thioalkoxy, aryloxy, and amine, wherein when n is other than 1, Rc and Rd in each (CRcRd) unit can be the same or different, and one or both Rc and Rd in one unit can form a 5-membered, 6-membered or 7-membered alicyclic, heteroalicyclic, aromatic or heteroaromatic ring with one or both Rc and Rd of an adjacent unit; and $R_{23}$-$R_{30}$ are each independently selected from the group consisting of hydrogen, alkyl, cycloalkyl, aryl, halo, alkoxy, aryloxy, trialkylsilyl, heteroalicyclic, heteroaryl and amine.

According to some of any of the embodiments described herein, at least one of $R_{23}$-$R_{26}$ is halo.

According to some of any of the embodiments described herein, at least one of $R_{24}$ and $R_{26}$ is halo.

According to some of any of the embodiments described herein, at least one of $R_{23}$-$R_{26}$ is a bulky rigid group.

According to some of any of the embodiments described herein, at least one of $R_{27}$-$R_{30}$ is other than hydrogen.

According to some of any of the embodiments described herein, at least one of $R_{27}$-$R_{30}$ is a heteroalicyclic or a heteroaryl.

According to some of any of the embodiments described herein, at least one of Ra-Rd is other than hydrogen.

According to some of any of the embodiments described herein, at least one of m and n is other than 1.

According to some of any of the embodiments described herein, the A bridging moiety has a general Formula A1, A2 or A3:

 Formula A1

 Formula A2

 Formula A3 wherein $R_5$-$R_{12}$, $R_{15}$ and $R_{16}$ are each independently selected from the group consisting of hydrogen, alkyl, cycloalkyl, aryl, heteroaryl and heteroalicyclic, $R_{13}$ and $R_{14}$ are each independently selected from the group consisting of hydrogen, alkyl, cycloalkyl, aryl, heteroaryl, heteroalicyclic, hydroxyl, alkoxy, thiol, thioalkoxy, aryloxy, and amine or, alternatively, at least two of $R_1$, $R_2$ and $R_5$-$R_6$ in Formula A1, or at least two of $R_1$, $R_2$ and $R_7$-$R_{10}$ in Formula A2 or at least two of $R_1$, $R_2$ and $R_{11}$-$R_{16}$ in Formula A3 form a 5 to 7-membered alicyclic, heteroalicyclic, aromatic or heterocyclic ring, and wherein when A has Formula A2, at least two of $R_1$, $R_2$ and $R_7$-$R_{10}$ do not form a heteroalicyclic ring.

According to some of any of the embodiments described herein, the bridging moiety has the Formula A2, and wherein each of $R_7$-$R_{10}$ is hydrogen.

According to some of any of the embodiments described herein, at least one, or both, of $R_1$ and $R_2$ is independently selected from alkyl, alkaryl and aryl.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 3A:
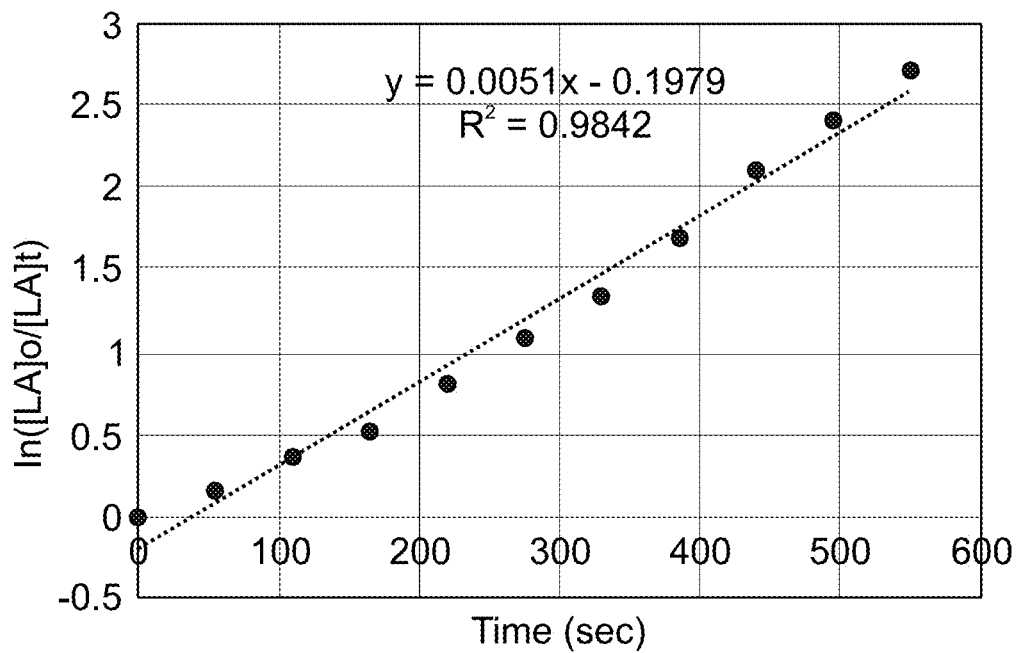
Figure 3B:
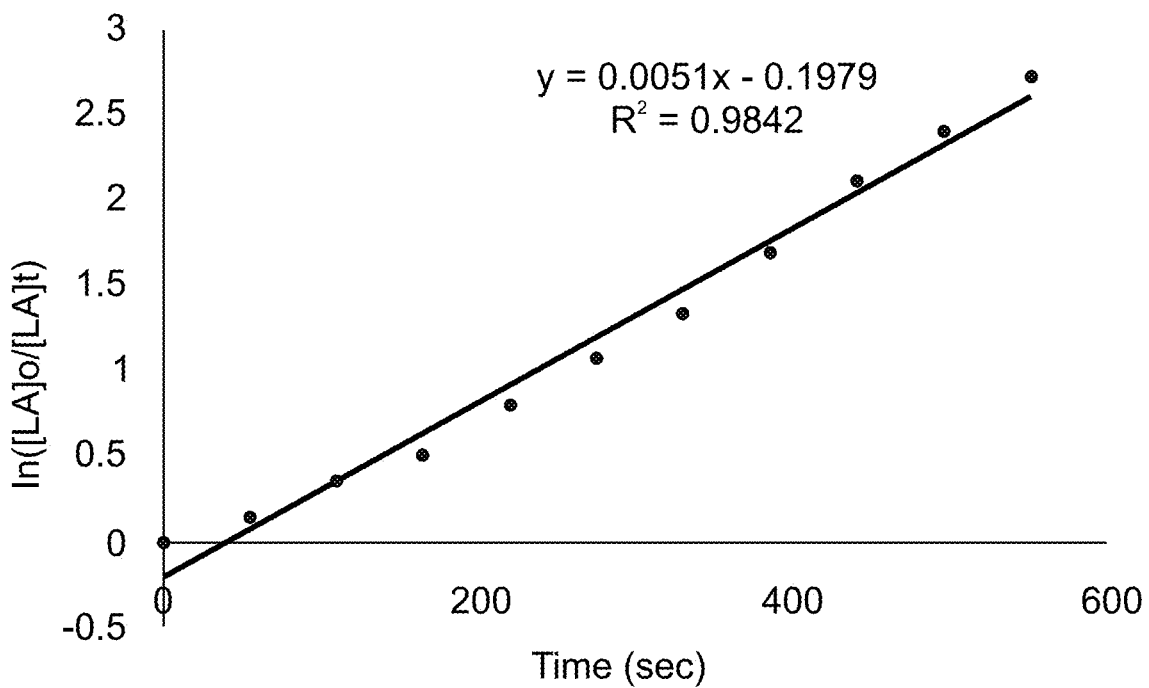
Figure 3C:
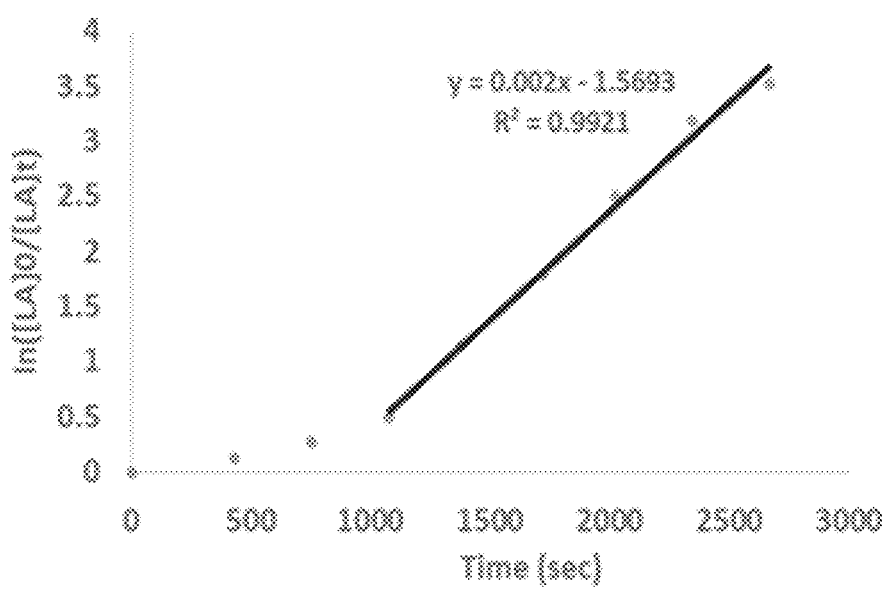
Figure 4B:
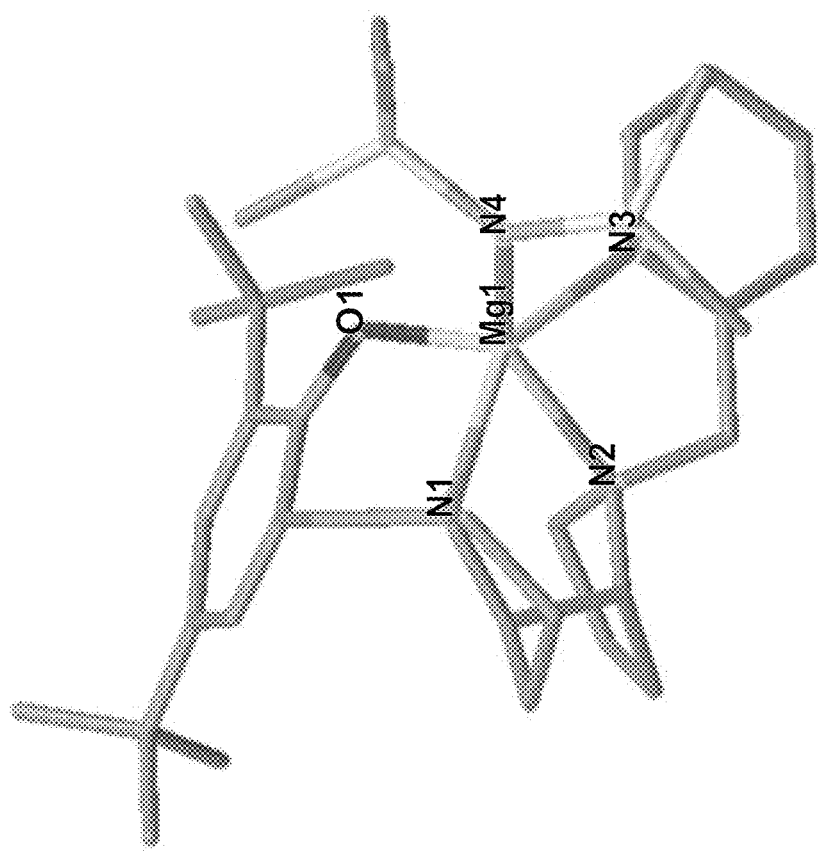
Figure 4A:
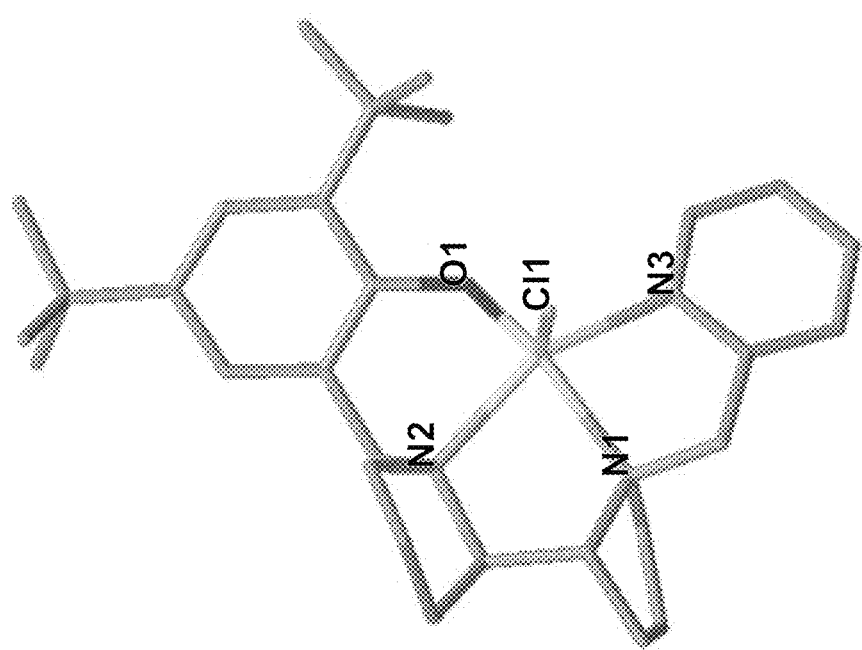

In the drawings:

FIG. 1 presents the chemical structures of exemplary tetradentate {ONNN}—H ligand precursors according to some embodiments of the present invention;

FIGS. 2A-C present molecular representations of the crystallographic structures of Lig$^1$Zn—Cl (FIG. 2A), Lig$^2$Zn-Et (FIG. 2B) and Lig$^3$Zn-Et (FIG. 2C);

FIGS. 3A-C present plots demonstrating a first-order kinetic of polymerization of rac-LA by (S,S)-Lig$^1$Zn-Et/BnOH (FIG. 3A), by (R,R)-Lig$^1$Zn-Et/BnOH (FIG. 3B) and by (R,R)-Lig$^2$Zn-Et/BnOH in dichloromethane-d2 at 298K; and FIGS. 4A-B present molecular representations of the crystallographic structures of Lig$^1$Mg—Cl (FIG. 4A), Lig$^2$Mg-HMDS (FIG. 4B).

DESCRIPTION OF SPECIFIC EMBODIMENTS OF THE INVENTION

The present invention, in some embodiments thereof, relates to chemistry and, more particularly, but not exclusively, to novel organometallic complexes, and to uses thereof in catalytic ring opening polymerization of cyclic esters.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

As discussed hereinabove, organometallic catalysts exhibiting stereochemical control of poly(lactic acid) obtained by ring opening polymerization (ROP) of lactide are extensively sought for.

Beyond the stereochemical control, such ROP catalysts should desirably exhibit high activity, and high turnover number and controlled or living character, the combination of which may give rise to PLA of high molecular weight. It is also preferable that the metal would be non-toxic and preferably biocompatible and that the ligand would be synthetically accessible and amenable to structural changes.

The present inventors have designed and successfully prepared and practiced a novel family of organometallic complexes based on sequential tetradentate monoanionic {ONNN}-type ligands. As demonstrated in the Examples section that follows, these complexes lead to highly active and very well-behaved catalysts, enabling the living as well as immortal ring opening polymerization of racemic lactide and homochiral lactide. These catalysts were shown to be isoselective by a fine interplay of chain-end and enantiomorphic-site control mechanisms.

Novel mononuclear organometallic complexes comprising sequential tetradentate (optionally pentadentate or higher) monoanionic {ONNN}-type ligands, and use of these complexes in the polymerization of cyclic esters such as lactides are disclosed herewith. The complexes as described herein are useful in isoselective polymerization of racemic mixtures of chiral cyclic esters such as lactides and lactones, to thereby obtain polyesters such as poly(lactic acid) (PLA) and poly-ε-caprolactone featuring high isotacticity. The complexes as described herein are useful in isoselective polymerization of racemic or meso cyclic esters such as lactide, to thereby obtain polyesters such as poly(lactic acid) featuring high stereoregularity.

Novel tetradentate monoanionic {ONNN}-type ligands usable for forming these complexes are also disclosed herewith.

The Organometallic Complexes:

According to an aspect of some embodiments of the present invention there is provided an organometallic complex represented by Formula I:

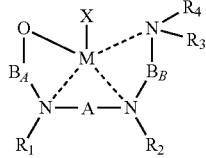

Formula I wherein:
the dashed line represents a coordinative bond;
M is a divalent metal;
X is a monoanionic ligand;
A, $B_A$ and $B_B$ are each independently a bridging moiety of 1 to 20 or of 1 to 12 carbon atoms;

$R_1$ and $R_2$ are each independently hydrogen, alkyl, cycloalkyl, aryl or alternatively, one or both of $R_1$ and $R_2$ form together, optionally with one or more carbon atoms in A, a heteroalicyclic or heteroaromatic, 5-, 6- or 7-membered ring; and $R_3$ and $R_4$ are each independently hydrogen, alkyl, cycloalkyl, aryl or alternatively, one or both of $R_3$ and $R_4$ form together with one or more carbon atoms in $B_B$, a heteroalicyclic or heteroaromatic, 5-, 6- or 7-membered ring.

By "divalent metal" it is meant a metal that has a valency of 2, that is, is capable of forming two covalent bonds with 2 monovalent atoms. A "divalent metal" encompasses also metals which feature also higher valency.

In some of any of the embodiments described herein, M is zinc, magnesium, or calcium. Other divalent metals are also contemplated. In some preferred embodiments, M is zinc.

In some preferred embodiments, M is magnesium.

The monoanionic ligand, X, can be, as non-limiting examples, alkyl (substituted or unsubstituted), cycloalkyl (substituted or unsubstituted), aryl (substituted or unsubstituted), amide, alkoxy, thioalkoxy, aryloxy, thioalryloxy, halo or amine (substituted or unsubstituted), as these terms are defined herein.

In some of any of the embodiments described herein for Formula I, M is zinc, and X is alkyl, alkaryl, cycloalkyl or aryl. In some of these embodiments, X is alkyl, preferably an unsubstituted alkyl, for example, ethyl. Other alkyls, preferably lower alkyls, are contemplated.

In some of any of the embodiments described herein for Formula I, M is magnesium and X is halo, for example chloro.

In some of any of the embodiments described herein for Formula I, M is magnesium and X is amine. In some of these embodiments, the amine is a substituted amine (e.g., a secondary or tertiary amine), (e.g., a mono- or di-substituted amine) and in some embodiments the amine is a tertiary amine, substituted by two substituents, as defined hereinunder for R and R".

In exemplary embodiments of Formula I, M is magnesium and X is an amine substituted by one or two silyl groups, as defined herein. In some of these embodiments, the one or two silyl groups are independently substituted, for example, by one or more alkyl groups.

In exemplary embodiments of Formula I, M is magnesium and X is bis-trimethylsilyl-amino of the formula: $[(CH_3)_3Si]_2N$—, which is also referred to herein and in the art as HMDS.

It is noted that when an amine is bound to a metal atom, the resulting moiety is also referred to herein and in the art as "amide", that is, a M-NR'R" moiety as described herein is also referred to herein and in the art as a metal amide (e.g., Mg-HMDS amide.

Any one of the bridging moieties, A, $B_A$ and $B_B$, independently, can be a hydrocarbon chain of the indicated number of carbon atoms, as defined herein.

Herein, the term "hydrocarbon" describes an organic moiety that includes, as its basic skeleton, a chain of carbon atoms, also referred to herein as a backbone chain, substituted mainly by hydrogen atoms. The hydrocarbon can be saturated or unsaturated, be comprised of aliphatic, alicyclic and/or aromatic moieties, and can optionally be substituted by one or more substituents (other than hydrogen). A substituted hydrocarbon may have one or more substituents, whereby each substituent group can independently be, for example, alkyl, cycloalkyl, alkenyl, alkynyl, alkaryl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, silyl, carbamate, amide, and hydrazine, and any other substituents as described herein.

In some embodiments, the hydrocarbon is substituted by one or more amine-containing groups, such as amide, alkyl, alkaryl, aryl or cycloalkyl substituted by one or more amine groups, an amine-containing heteroalicyclic, and/or an amine-containing heteroaryl.

The hydrocarbon moiety can optionally be interrupted by one or more heteroatoms, including, without limitation, one or more oxygen, nitrogen (substituted or unsubstituted, as defined herein for —NR'—) and/or sulfur atoms.

In some embodiments of any of the embodiments described herein the hydrocarbon is not interrupted by any heteroatom, nor does it comprise heteroatoms in its backbone chain, and can be an alkylene chain, or be comprised of alkyls, cycloalkyls, aryls, alkenes and/or alkynes, covalently attached to one another in any order.

In some of any of the embodiments described herein, the hydrocarbon is an alkylene chain, which can be unsubstituted or substituted, as described herein.

In some of any of the embodiments described herein, the $B_A$ bridging moiety has a general Formula:

—(CRaRb)$m$-C(R$_{17}$R$_{18}$)—C(R$_{19}$R$_{20}$)— wherein:

m is an integer of from 1 to 6, or from 1 to 4, or from 1 to 2;

Ra and Rb are each independently hydrogen, alkyl, cycloalkyl, aryl, heteroaryl, heteroalicyclic, hydroxyl, alkoxy, thiol, thioalkoxy, aryloxy, and amine, wherein when m is other than 1, Ra and Rb in each (CRaRb) unit can be the same or different, and one or both Ra and Rb in one unit can form a 5-, 6- or 7-membered alicyclic, heteroalicyclic, aromatic or heteroaromatic ring with one or both Ra and Rb of an adjacent unit; and $R_{17}$-$R_{20}$ are each independently hydrogen, alkyl, cycloalkyl, aryl, heteroaryl, heteroalicyclic, hydroxyl, alkoxy, thiol, thioalkoxy, aryloxy, and amine, or, alternatively, two or more of $R_{17}$-$R_{20}$ form together a 5-, 6- or 7-membered alicyclic, heteroalicyclic, aromatic or heteroaromatic ring.

In some of these embodiments m is 1.

In some of any of the embodiments of $B_A$ of the above formula, Ra and Rb are each hydrogen.

In some of any of the embodiments of $B_A$ of the above formula, $R_{17}$-$R_{20}$ form together a substituted or unsubstituted, preferably 6-membered, aromatic ring.

In some of any of the embodiments of $B_A$ of the above formula, $R_{17}$-$R_{20}$ form together with the oxygen attached to $B_A$ a substituted or unsubstituted phenolate group.

In some of any of the embodiments described herein, the $B_B$ bridging moiety has a general Formula:

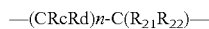
—(CRcRd)$n$-C(R$_{21}$R$_{22}$)— wherein:

n is an integer of from 1 to 6, or from 1 to 4, or from 1 to 2;

Rc and Rd are each independently hydrogen, alkyl, cycloalkyl, alkaryl, aryl, heteroaryl, heteroalicyclic, hydroxyl, alkoxy, thiol, thioalkoxy, aryloxy, and amine, wherein when n is other than 1, Rc and Rd in each (CRcRd) unit can be the same or different, and one or both Rc and Rd in one unit can form a 5-, 6- or 7-membered alicyclic, heteroalicyclic, aromatic or heteroaromatic ring with one or both Rc and Rd of an adjacent unit; and $R_{21}$ and $R_{22}$ are each independently hydrogen, alkyl, cycloalkyl, aryl, heteroaryl, heteroalicyclic, hydroxyl, alkoxy, thiol, thioalkoxy, aryloxy, and amine, or, alternatively, at least two of $R_3$, $R_4$, $R_{21}$ and $R_{22}$ form together a 5, 6- or 7-membered heteroalicyclic or heteroaromatic ring (which includes, as a heteroatom, at least the nitrogen to which $B_B$ is attached, thus forming a nitrogen-containing heteroalicyclic or heteroaryl, as described herein).

In some of any of these embodiments, n is 1.

In some of any of these embodiments, Rc and Rd are each hydrogen.

In some of any of these embodiments, $R_3$, $R_4$, $R_{21}$ and $R_{22}$ form together a substituted or unsubstituted, preferably 6-membered, heteroaromatic ring, for example, a nitrogen-containing hereteroayl, as described herein. In some of these embodiments, the heteroaryl is pyridine, which is connected to (CRcRd)n at the ortho position. Other heteroaryls, or heteroalicyclics, and other attachment positions are also contemplated.

In some of any of the embodiments described herein, the complex is represented by Formula IA:

Formula IA

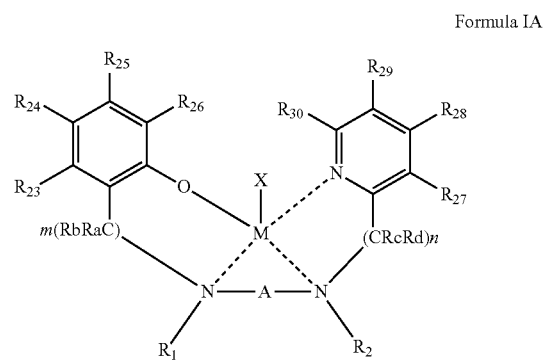

wherein M, X, A, $R_1$, $R_2$, n, m, and Ra-Rd, are as defined herein in any of the respective embodiments, and $R_{23}$-$R_{30}$ are each independently selected from the group consisting of hydrogen, alkyl, cycloalkyl, alkaryl, aryl, halo, alkoxy, aryloxy, silyl (e.g., trialkylsilyl), heteroalicyclic, heteroaryl, and amine, and any of the other substituents described herein.

In some of any of the embodiments pertaining to Formula IA, at least one of $R_{23}$-$R_{26}$ is alkyl.

In some of any of the embodiments pertaining to Formula IA, at least one of $R_{24}$ and $R_{26}$ is alkyl.

In some of any of the embodiments pertaining to Formula IA, the alkyl is a bulky alkyl such as, but not limited to, tert-butyl, isobutyl, isopropyl, trityl, cumyl and tert-hexyl.

As used herein, the phrase "bulky", in the context of a group or an alkyl in particular, describes a group that occupies a large volume. A bulkiness of a group or an alkyl is determined by the number and size of the atoms composing the group, by their arrangement, and by the interactions between the atoms (e.g., bond lengths, repulsive interactions). Typically, lower, linear alkyls are less bulky than branched alkyls; bicyclic molecules are more bulky than cycloalkyls, etc.

Exemplary bulky alkyls include, but are not limited to, branched alkyls such as tert-butyl, isobutyl, isopropyl and tert-hexyl, as well as substituted alkyls such as triphenylmethane (trityl) and cumyl.

In some of any of the embodiments pertaining to Formula IA, at least one of $R_{23}$-$R_{26}$ is independently a halo, for example, chloro, bromo or iodo, preferably chloro.

In some of any of the embodiments pertaining to Formula IA, at least one of $R_{24}$ and $R_{26}$ is halo (e.g., chloro).

In some of any of the embodiments pertaining to Formula IA, at least one of $R_{23}$-$R_{26}$ is a bulky rigid group.

The bulky rigid group can be, for example, aryl, heteroaryl, cycloalkyl and heteroalicyclic, having at least 7 carbon atoms.

As used herein, the phrase "bulky rigid group" describes a bulky group, as defined herein, with reduced number of free-rotating bonds. Such a group, unlike bulky alkyls, are rigid in terms of free rotation. Exemplary bulky rigid groups that are suitable for use in the context of embodiments of the invention include, but are not limited to, aryl, heteroaryl, cycloalkyl and/or heteroalicyclic, as defined herein.

In some embodiments, the rigid bulky group is such that has a total of 7 carbon atoms or more, each being substituted or unsubstituted.

In some embodiments, the bulky rigid group is a bicyclic group, comprising two or more of a cycloalkyl, aryl, heteroalicyclic or heteroaryl fused or linked to one another.

An exemplary bulky rigid group is adamantyl, for example, 1-adamantyl.

In some of any of the embodiments pertaining to Formula IA, $R_{26}$ is a bulky rigid group, as defined herein, for example, 1-adamantyl.

In some of any of the embodiments pertaining to Formula IA, each of $R_{27}$-$R_{30}$ is hydrogen, although any other substituents are contemplated.

In some of any of the embodiments pertaining to Formula IA, at least one of $R_{27}$-$R_{30}$ is a heteroalicyclic or a heteroaryl, preferably a nitrogen-containing heteroalicyclic or heteroaryl, as described herein. In some of these embodiments, the additional nitrogen atom also coordinates with the metal atom M, such the complex comprises a pentadentate ligand.

In some of any of the embodiments pertaining to Formula IA, $R_{30}$ is a nitrogen-containing heteroaryl, and in some of these embodiments, the complex comprises a pentadentate ligand.

In some of any of the embodiments described herein for Formula I or IA, $R_1$ and $R_2$ can be the same or different and each is independently an alkyl, an aryl or an alkaryl (e.g., benzyl). In exemplary embodiments, $R_1$ and $R_2$ are each alkyl, for example, are each methyl. In exemplary embodiments, $R_1$ and $R_2$ are each alkaryl, for example, benzyl.

In some of any of the embodiments described herein for Formula I or IA, one or both of $R_1$ and $R_2$ form together with one or more carbon atoms in A, a heteroalicyclic 5-, 6- or 7-membered ring.

In some of any of the embodiments described herein for Formula I or IA, at least one of $R_1$ and $R_2$ do/does not form together with one or more carbon atoms in A, a heteroalicyclic 5-, 6- or 7-membered ring.

In some of any of the embodiments described herein for Formula I or IA, at least one of $R_1$ and $R_2$ do/does not form together with one or more carbon atoms in A, a pyrrolidone ring.

In some of any of the embodiments described herein for Formula I or IA, A is other than bispyrrolidone.

In some of any of the embodiments described herein, for Formula I and IA, the A bridging moiety has a general Formula A1, A2 or A3:

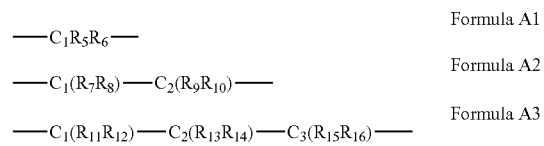

wherein $R_5$-$R_{12}$, $R_{15}$ and $R_{16}$ are each independently selected from the group consisting of hydrogen, alkyl, cycloalkyl, aryl, heteroaryl and heteroalicyclic, $R_{13}$ and $R_{14}$ are each independently selected from the group consisting of hydrogen, alkyl, cycloalkyl, aryl, heteroaryl, heteroalicyclic, hydroxyl, alkoxy, thiol, thioalkoxy, aryloxy, and amine or any of the other substituents described herein, or, alternatively, at least two of $R_1$, $R_2$ and $R_5$-$R_6$ in Formula A1, or at least two of $R_1$, $R_2$ and $R_7$-$R_{10}$ in Formula A2 or at least two of $R_1$, $R_2$ and $R_{11}$-$R_{16}$ in Formula A3 form a 5-, 6- or 7-membered alicyclic, heteroalicyclic, aromatic or heterocyclic ring.

In some of any of the embodiments described herein, in formula A1, each of $R_5$ and $R_6$ is hydrogen, that is, A is methylene.

In some of any of the embodiments described herein, in formula A2, each of $R_7$-$R_{10}$ is hydrogen, that is, A is ethylene.

In some of any of the embodiments described herein, in formula A3, each of $R_{11}$-$R_{16}$ is hydrogen, that is, A is propylene.

In some of the embodiments where the bridging moiety A is an alkylene chain (methylene, ethylene or propylene), $R_1$ and $R_2$ can be the same or different and each is independently an alkyl, an aryl or an alkaryl (e.g., benzyl). In exemplary embodiments, $R_1$ and $R_2$ are each alkyl, for example, are each methyl. In exemplary embodiments, $R_1$ and $R_2$ are each alkaryl, for example, benzyl.

In some of any of the embodiments described herein, the bridging moiety has the Formula A2.

In some of any of the embodiments described herein, in formula A2, each of $R_7$-$R_{10}$ is hydrogen. In some of these embodiments, $R_1$ and $R_2$ can be the same or different and each is independently an alkyl, an aryl or an alkaryl (e.g., benzyl). In exemplary embodiments, $R_1$ and $R_2$ are each alkyl, for example, are each methyl. In exemplary embodiments, $R_1$ and $R_2$ are each alkaryl, for example, benzyl.

In some of any of the embodiments described herein, in formula A2, $R_7$ and $R_{10}$ form the heteroalicyclic ring, for example, a pyrrolidine.

Alternatively, or in addition, in some embodiments, $R_9$ and $R_2$ form the heteroalicyclic ring, for example, a pyrrolidine.

In some of any of the embodiments described herein for formula A2, the bridging moiety is bipyrrolidine.

In some of any of the embodiments described herein, at least one, or both, of $R_1$ and $R_2$ is independently an alkyl, for example, methyl.

In some of any of the embodiments described herein for an organometallix complex, a metal atom M bound to X, as described herein for any of the embodiments of Formula I or IA, is in coordination with a ligand derives from a ligand precursor compound as described hereinafter, in any of the respective embodiments of the ligand precursor compound.

Exemplary, non-limiting examples of complexes according to the present embodiments are presented in the Examples section that follows.

The Polymerization Process:

According to an aspect of some embodiments of the present invention, there is provided a process of ring opening polymerization of a cyclic ester, the process comprising contacting the cyclic ester with a catalyst system that comprises an organometallic complex as described herein in any of the respective embodiments.

The organometallic complex as described herein in any of the respective embodiments is also referred to herein as a "catalyst" or, in some embodiments, as a "pre-catalyst", which is activated by a co-catalyst as described herein. In some of any of the embodiments described herein, the catalyst system further comprises a co-catalyst.

The "co-catalyst" described herein is also referred to herein and in the art as "initiator".

In some embodiments the initiator is a hydroxy-containing compound.

The hydroxy-containing compound can feature one hydroxy group, and can be, for example, HO-Rk, wherein Rk is alkyl, alkaryl, cycloalkyl or aryl.

Exemplary such initiators include, without limitation, benzyl alcohol, and alkyl alcohols such as ethyl alcohol, methyl alcohol, 2-propyl alcohol, tert-butyl alcohol, monohydroxy terminated polyethylene glycol, and monohydroxy terminated pre-synthesized polymers.

The hydroxy-containing compound can feature two or more hydroxy groups, and such compounds are also referred to herein and in the art as polyhydroxy compounds.

Exemplary such compounds include, but are not limited to, alkylene glycols (featuring 2 hydroxy groups, for example, ethylene glycol, propylene glycol, etc., as glycerols (featuring 3 hydroxy groups), higher linear saccharides, and polyhydroxy compounds such poly(ethylene glycol) or pentaerythritol.

The type of initiator, namely, the number of the hydroxy groups in the initiator determines the number of the polymeric chains in a polymerized cyclic ester.

A mol ratio of the cyclic ester and the initiator determines the number of backbone units in each polymeric chain.

Thus, the polymer architecture (e.g., number and length of the polymeric chains) can be determined or controlled as desired by using an initiator that provides for the desirable properties. In some of any of the embodiments described herein, the catalyst system does not comprise a co-catalyst, and in some of these embodiments, the catalyst system consists of the organometallic complex. In some of these embodiments, M in Formula I or IA is magnesium (Mg). In some of these embodiments, X in Formula I or IA is halo (e.g., chloro). In some of these embodiments, X in Formula I or IA is a substituted amine, as described herein, for example, HMDS.

In some of any of the embodiments described herein, the contacting is at room temperature.

In some of any of the embodiments described herein, the contacting is in a solution (e.g., in an organic solvent). In some embodiments, the organic solvent is a polar solvent, for example, having a polarity index higher than 1, or higher than 2, or higher than 3, and in some embodiments, it is a polar aprotic solvent. In some embodiments, the organic solvent is devoid of heteroatoms that can coordinate the metal atom, such as oxygen and nitrogen.

Exemplary solvents include, but not limited to, dichloromethane (DCM), chlorobenzene, tetrahydrofuran (THF), diethylether, ethylene dichloride, toluene, pentane, and the like.

In some of any of the embodiments described herein, the contacting is in a melt, that is, is devoid of a solvent and is performed at a temperature at which the cyclic ester is liquid, for example, at a temperature which is at least the melting temperature of the cyclic ester, or is higher than the melting temperature of the cyclic ester by, for example, 5, 10, 15, 20 or more ° C.

In some of any of the embodiments described herein, the contacting is effected under inert environment.

By "inert environment" it is meant an environment that is substantially free of oxygen, carbon dioxide, water and/or any other substances that may chemically react with the organometallic complex or otherwise interfere in the polymerization reaction.

In some of any of the embodiments described herein, the contacting is for a time period that ranges from 1 second to 24 hours, or from 1 second to 12 hours, or from 1 second to 5 hours, or from 10 seconds to 5 hours, or from 30 seconds to 5 hours, or from 30 seconds to 3 hours, of from 30 seconds to 2 hours, including any intermediate values and subranges therebetween.

In some of any of the embodiments described herein, the contacting is effected as a single batch, that is, a cyclic ester, or a mixture of two or more cyclic esters, are contacted with the catalyst system all together in a single batch, simultaneously (and not sequentially).

In some of any of the embodiments described herein, a mol ratio of the cyclic ester and the organometallic complex ranges from 10:1 to 100000:1, or from 100:1 to 100000:1, or from 100:1 to 10000:1, including any intermediate values and subranges therebetween.

In some of any of the embodiments described herein, a mol ratio of the organometallic complex and the co-catalyst (if present) ranges from 1000:1 to 1:1000, or from 100:1 to 1:100, or from 10:1 to 1:1000, or from 10:1 to 1:100, or from 10:1 to 1:50, or from 10:1 to 1:40 or from 10:1 to 1:30, or from 10:1 to 1:20 or from 10:1 to 1:10, or from 1:1 to 1:10, or from 1:1 to 1:8, or from 1:1 to 1:6, or from 1:1 to 1:5 or from 1:1 to 1:4, including any intermediate values and subranges therebetween.

In some of any of the embodiments described herein, the polymerization is a living polymerization.

By "living polymerization", as used herein, it is meant a form of chain growth polymerization where chain termination is very low, the molecular weight of the polymer is proportional to the conversion, and the molecular weight distribution, PDI (polydispersity index), is very narrow.

In some of any of the embodiments described herein, the polymerization is an immortal polymerization.

Immortal polymerization, as used herein, is a form of living chain growth polymerization where the number of polymer chains is higher than the number of catalyst molecules and all polymer chains can grow by the catalyst. For example, by employing a ratio of a co-catalyst to living catalyst higher than 1 the number of polymer chains will be higher than the number of catalyst molecules and identical to the number of co-catalyst molecules. As a result, immortal polymerization can afford polymers with a controlled molecular weight, while the number of polymer molecules is higher than the number of the catalyst molecules.

The Cyclic Ester and the Polyester:

The term "cyclic ester" as used herein describes a —C(=O)—O—Rx in which Rx is an hydrocarbon chain (e.g., lower, medium or higher alkyl, optionally substituted), as defined herein, optionally interrupted by one or more heteroatoms or moieties as defined herein, and one carbon atom of the hydrocarbon chain (e.g., of an alkyl) is linked to the carbon atom of the carboxylate to form a ring.

In some embodiments, a cyclic ester can be represented by Formula III:

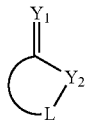

Formula III wherein:

$Y_1$ and $Y_2$ are each independently selected from oxygen and sulfur; and

L is a hydrocarbon chain, for example, a hydrocarbon chain which comprises one or more alkylene chains, each optionally being independently substituted or unsubstituted, and which can optionally be interrupted therebetween by one or more moieties such as oxygen atom, sulfur atom, amine, silyl, carbonyl, amide, carboxy (—C(=O)—O—), thiocarboxy, thiocarbonyl, and the like.

Each alkylene chain can be of from 1 to 30 carbon atoms, preferably from 1 to 20 carbon atoms, or from 1 to 15 carbon atoms, or from 1 to 10 carbon atoms.

In some of any of the embodiments described herein, the cyclic ester comprises two or more alkylene chains, which are interrupted therebetween, wherein at least two alkylene chains are interrupted therebetween by a carboxy group. Such cyclic esters are also referred to herein and in the art as "cyclic diesters".

In some of any of the embodiments described herein, the one or more alkylene chain(s) is/are unsubstituted.

In some of any of the embodiments described herein, at least one of $Y_1$ and $Y_2$ is oxygen.

In some of any of the embodiments described herein, each of $Y_1$ and $Y_2$ is oxygen.

In some of any of the embodiments described herein, L is an alkylene chain, non-interrupted. Such cyclic esters are also referred to herein and in the art as "lactone".

In some of any of the embodiments described herein, L comprises two alkylene chains, interrupted by a carboxy group, whereby the two alkylene chains are identical to one another. Such a cyclic diester can also be regarded as a di-lactone of two molecules of a 2-hydroxycarboxylic acid, and is also referred to in the art as lactide.

While the term "lactide" generally describes a di-lactone of any 2-hydroxycarboxylic acid, herein and in the art, this term typically also refers to a cyclic di-ester (di-lactone) of lactic acid (2-hydroxypropionic acid), as shown, for example, in Scheme 1 hereinabove.

Cyclic esters usable in the context of the present embodiments include substituted and unsubstituted lactones such as, for example, caprolactones and lactides, although any other cyclic esters are contemplated, for example, δ-valerolactone, γ-butyrolactone, ε-caprolactone, ω-pentadecalactone, cyclopentadecanone, 16-hexadecanolide, oxacyclotridecan-2-one.

In some of any of the embodiments described herein, the cyclic ester is lactide, that is, a di-lactone of of lactic acid (2-hydroxypropionic acid).

In some of any of the embodiments described herein, the cyclic ester is a lactone, for example, a caprolactone such as ε-caprolactone.

In some of any of the embodiments described herein, the cyclic ester is a lactone, for example, caprolactone such as ε-caprolactone, and the process of polymerization comprises contacting the lactone with a catalyst of Formula I or IA as described herein, wherein M is magnesium. In some of these embodiments, X in Formula I or IA is an amine substituted by one or silyl groups, as described herein.

In some of any of the embodiments described herein, the cyclic ester has a chiral center.

Herein a "chiral cyclic ester" or a "cyclic ester having a chiral center", typically describes a cyclic ester or a cyclic diester as defined herein, in which one or more carbon atoms in one or more of the alkylene chains is substituted and thereby form a chiral center. Whenever these phrases are used, the cyclic ester can be one enantiomer, one diastereomer, a meso form, or a racemic mixture, unless otherwise indicated.

In some of these embodiments, the cyclic ester is a racemic cyclic ester.

In some of any of the embodiments described herein, the cyclic ester is lactide and the lactide is a homochiral lactide or a racemic lactide or a meso lactide.

In some of any of the embodiments described herein, the lactide is a racemic lactide.

In some of any of the embodiments described herein, the polymerization is an isoselective polymerization (e.g., in case the cyclic ester is chiral). By "isoselective polymerization", it is meant a stereo-controlled polymerization that provides at least one enchainment of an identical enantiomer or diastereomer. Isoselective polymerization can provide a polymer comprising backbone units that feature generally (e.g., at least 60%, or at least 70%, or at least 80%, or more) the same stereoconfiguration, that is a single enchainment of an identical enantiomer or diastereomer, or a mixture of two such polymers (for example, one of an R enantiomer and the other of an S enantiomer).

Isoselective polymerization can be determined by the Pm of the obtained polymer.

Herein and in the art, Pm describes the tendency for a meso-enchainment (i.e. identical enantiomer enchainment) in polymerization of a cyclic ester having one or more chiral centers, which gives rise to isotactic polyester. A Pm value of 1.0 corresponds to perfectly isotactic polyester and a Pm value of 0.5 or lower corresponds to atactic PLA. A Pm value higher than 0.6, or higher than 0.7 is indicative of an isoselective polymerization.

According to an aspect of some embodiments of the present invention there is provided a polyester obtainable by a process as described herein in any of the respective embodiments.

In some of any of the embodiments described herein, the polyester is characterized by a polydispersity (Mw/Mn) lower than 3, or lower than 2, or lower than 1.5, or lower than 1.2.

In some of any of the embodiments described herein, the cyclic ester is a racemic mixture of a chiral cyclic ester, and the polyester obtained by the ROP is characterized by Pm of at least 0.6, or at least 0.7, or at least 0.8, while higher values are also contemplated.

In some of any of the embodiments described herein, the polyester is formed of a cyclic ester which is lactide, as described herein, for example, racemic lactide (rac-lactide). In some of these embodiments, the polyester is an isotactic PLA.

According to an aspect of some embodiments of the present invention there is provided an article-of-manufacturing comprising a polyester as described herein, for example, a poly(lactic acid) (PLA). Any articles commonly containing PLA and/or are contemplated, as representative, non-limiting examples. Examples include, without limitation, commodity articles like food packaging, fibers, tubes, non-woven fabrics, etc. and articles employed in biomedical applications like resorbable coronary stents, matrices for controlled drug release, implants, sutures, etc.

The Ligand Precursor:

According to an aspect of some embodiments of the present invention, there is provided a compound represented by Formula II:

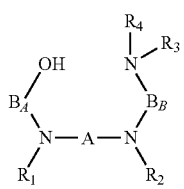

Formula II wherein:

A, $B_A$, $B_B$, and $R_1$-$R_4$ are as described herein in any of the embodiments pertaining to an organometallic complex.

Compounds represented by Formula II, as described herein in any of the respective embodiments, are usable as ligand precursors for forming an organometallic complex represented by Formula I or IA, as described herein in any of the respective embodiments, and are therefore also referred to herein interchangeably as "ligand precursor compounds", "ligand precursors" or simply as "ligands" or "ligand compounds". In some of any of the embodiments described herein for a ligand precursor, the compound is other than (2,4-di-tert-butyl-6-(((2S,2'S)-1'-(pyridin-2-ylmethyl)-[2,2'-bipyrrolidin]-1-yl)methyl)phenol).

In some of any of the embodiments described herein for a ligand precursor, the compound is such that:

(i) when $R_3$ and $R_4$ from together with $B_B$ an unsubstituted 6-membered heteroatomic ring, $B_A$ is other than benzyl; or (ii) when $R_3$ and $R_4$ from together with $B_B$ an unsubstituted 6-membered heteroatomic ring and/or $B_A$ is benzyl, A is a bridging moiety of 1 or of 3 to 12 carbon atoms; or (iii) when $R_3$ and $R_4$ from together with $B_B$ an unsubstituted 6-membered heteroatomic ring and/or $B_A$ is benzyl, at least one of $R_1$ and $R_2$ do not form together with carbon atoms in A a heteroalicyclic 5-membered ring; or (iv) when $R_3$ and $R_4$ from together with $B_B$ an unsubstituted 6-membered heteroatomic ring; each of $R_1$ and $R_2$ form together with carbon atoms in A a heteroalicyclic 5-membered ring; and $B_A$ is benzyl, said benzyl is substituted by at least one halo and/or at least one bulky rigid group; or (v) when $B_A$ is benzyl; and each of $R_1$ and $R_2$ form together with carbon atoms in A a heteroalicyclic 5-membered ring; and $R_3$ and $R_4$ from together with $B_B$ a 6-membered heteroatomic ring, said heteroaromatic ring is substituted.

In some of any of the embodiments described herein, the ligand precursor compound is represented by Formula IIA:

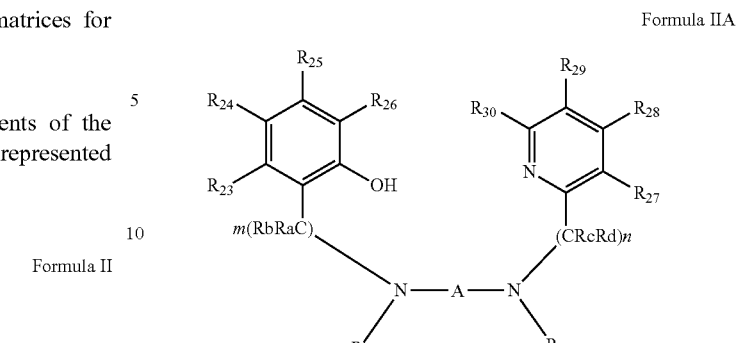

Formula IIA wherein:

Ra, Rb, Rc, Rd, and $R_{23}$-$R_{30}$ are as defined herein in any of the embodiments pertaining to an organometallic complex.

In some of any of the embodiments described herein in the context of the ligand precursor of Formula IIA, at least one of $R_{23}$-$R_{26}$ is halo, as described herein In some of any of the embodiments described herein in the context of the ligand precursor of Formula IIA, at least one of $R_{24}$ and $R_{26}$ is halo, as described herein.

In some of any of the embodiments described herein in the context of the ligand precursor of Formula IIA, at least one of $R_{23}$-$R_{26}$ is a bulky rigid group, as described herein.

In some of any of the embodiments described herein in the context of the ligand precursor of Formula IIA, $R_{26}$ is a bulky rigid group, for example, adamantyl, as described herein.

In some of any of the embodiments described herein in the context of the ligand precursor of Formula IIA, at least one of $R_{27}$-$R_{30}$ is other than hydrogen.

In some of any of the embodiments described herein in the context of the ligand precursor of Formula IIA, at least one of $R_{27}$-$R_{30}$ is a heteroalicyclic or a heteroaryl, as described herein.

In some of any of the embodiments described herein in the context of the ligand precursor of Formula IIA, $R_{30}$ is a nitrogen-containing heteroaryl, and in some embodiments, such a ligand precursor forms a pentadentate ligand.

In some of any of the embodiments described herein in the context of the ligand precursor of Formula IIA, at least one of Ra-Rd is other than hydrogen.

In some of any of the embodiments described herein in the context of the ligand precursor of Formula IIA, at least one of m and n is other than 1.

In some of any of the embodiments described herein in the context of the ligand precursor of Formula II or IIA, the A bridging moiety has a general Formula A1, A2 or A3:

Formula A1

Formula A2

Formula A3 wherein $R_5$-$R_{12}$, $R_{15}$ and $R_{16}$ are each independently selected from the group consisting of hydrogen, alkyl, cycloalkyl, aryl, heteroaryl and heteroalicyclic, $R_{13}$ and $R_{14}$ are each independently selected from the group consisting of hydrogen, alkyl, cycloalkyl, aryl, heteroaryl, heteroalicyclic, hydroxyl, alkoxy, thiol, thioalkoxy, aryloxy, and amine or, alternatively, at least two of $R_1$, $R_2$ and $R_5$-$R_6$ in Formula A1, or at least two of $R_1$, $R_2$ and $R_7$-$R_{10}$ in Formula A2 or at least two of $R_1$, $R_2$ and $R_{11}$-$R_{16}$ in Formula A3 form a 5-, 6- or 7-membered alicyclic, heteroalicyclic, aromatic or heterocyclic ring.

In some of any of the embodiments described herein in the context of the ligand precursor of Formula II or IIA, the A bridging moiety has a general Formula A1 or A3, as described herein.

In some of any of the embodiments described herein in the context of the ligand precursor of Formula II or IIA, in formula A1, each of $R_5$ and $R_6$ is hydrogen, that is, A is methylene.

In some of any of the embodiments described herein in the context of the ligand precursor of Formula II or IIA, in formula A2, each of $R_7$-$R_{10}$ is hydrogen, that is, A is ethylene.

In some of any of the embodiments described herein in the context of the ligand precursor of Formula II or IIA, in formula A3, each of $R_{11}$-$R_{16}$ is hydrogen, that is, A is propylene.

In some of the embodiments described herein in the context of the ligand precursor of Formula II or IIA where the bridging moiety A is an alkylene chain (methylene, ethylene or propylene), $R_1$ and $R_2$ can be the same or different and each is independently an alkyl, an aryl or an alkaryl (e.g., benzyl). In exemplary embodiments, $R_1$ and $R_2$ are each alkyl, for example, are each methyl. In exemplary embodiments, $R_1$ and $R_2$ are each alkaryl, for example, benzyl.

In some of any of the embodiments described herein described herein in the context of the ligand precursor of Formula II or IIA, the bridging moiety has the Formula A2.

In some of any of the embodiments described herein in the context of the ligand precursor of Formula II or IIA, in formula A2, each of $R_7$-$R_{10}$ is hydrogen. In some of these embodiments, $R_1$ and $R_2$ can be the same or different and each is independently an alkyl, an aryl or an alkaryl (e.g., benzyl). In exemplary embodiments, $R_1$ and $R_2$ are each alkyl, for example, are each methyl. In exemplary embodiments, $R_1$ and $R_2$ are each alkaryl, for example, benzyl. In some of any of the embodiments described herein in the context of the ligand precursor of Formula II or IIA, when A has Formula A2, at least two of $R_1$, $R_2$ and $R_7$-$R_{10}$ do not form a heteroalicyclic ring.

In some of any of the embodiments described herein in the context of the ligand precursor of Formula II or IIA, when A has Formula A2, A is other than bipyrrolidine.

In some of any of the embodiments described herein in the context of the ligand precursor, the bridging moiety has the Formula A2, and each of $R_7$-$R_{10}$ is hydrogen.

In some of any of the embodiments described herein in the context of the ligand precursor, at least one, or both, of $R_1$ and $R_2$ is alkyl.

According to further aspects of the present invention there are provided processes of preparing the ligand precursor compounds and complexes made therefrom, which are effected substantially in accordance with the processes described in the Examples section that follows, while selecting suitable starting materials and reactants.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein throughout, the phrase "linking moiety" or "linking group" describes a group that connects two or more moieties or groups in a compound. A linking moiety is typically derived from a bi- or tri-functional compound, and can be regarded as a bi- or tri-radical moiety, which is connected to two or three other moieties, via two or three atoms thereof, respectively.

Exemplary linking moieties include a hydrocarbon moiety or chain, optionally interrupted by one or more heteroatoms, as defined herein, and/or any of the chemical groups listed below, when defined as linking groups.

When a chemical group is referred to herein as "end group" it is to be interpreted as a substituent, which is connected to another group via one atom thereof.

Herein throughout, the term "hydrocarbon" collectively describes a chemical group composed mainly of carbon and hydrogen atoms. A hydrocarbon can be comprised of alkyl, alkene, alkyne, aryl, and/or cycloalkyl, each can be substituted or unsubstituted, and can be interrupted by one or more heteroatoms. The number of carbon atoms can range from 2 to 20, and is preferably lower, e.g., from 1 to 10, or from 1 to 6, or from 1 to 4. A hydrocarbon can be a linking group or an end group.

Bisphenol A is An example of a hydrocarbon comprised of 2 aryl groups and one alkyl group.

As used herein, the term "amine" describes both a —NR'R" group and a —NR'— group, wherein R' and R" are each independently hydrogen, alkyl, cycloalkyl, aryl, alkaryl, heteroaryl, heteroalicyclic, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, alkenyl, alkynyl, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, silyl, guanyl, guanidine and hydrazine.

The term "amine" is used herein to describe a —NR'R" group in cases where the amine is an end group, as defined hereinunder, and is used herein to describe a —NR'— group in cases where the amine is a linking group or is or part of a linking moiety.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 6, or 1 to 4 carbon atoms (C(1-4) alkyl). The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, silyl, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain. When the alkyl is a linking group, it is also referred to herein as "alkylene" or "alkylene chain".

Alkene (or alkenyl) and Alkyne (or alkynyl), as used herein, are an alkyl, as defined herein, which contains one or more double bond or triple bond, respectively.

The term "cycloalkyl" describes an all-carbon monocyclic ring or fused rings (i.e., rings which share an adjacent pair of carbon atoms) group where one or more of the rings does not have a completely conjugated pi-electron system. Examples include, without limitation, cyclohexane, adamantine, norbornyl, isobornyl, and the like. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, alkaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, silyl, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofuran, tetrahydropyrane, morpholine, oxalidine, and the like. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, alkaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, silyl, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, alkaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, silyl, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, alkaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, silyl, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, pyrrolidone, oxazole, indole, purine and the like.

The term "piperazine" refers to

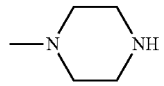

a group or a

or a

group, where R' and R" are as defined hereinabove.

The term "piperidine" refers to a

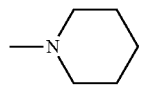

group or a

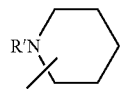

group, with R' as defined herein.

The term "pyrrolidine" refers to a

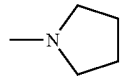

group or a

group, with R' as defined herein.

The term "pyridine" refers to a

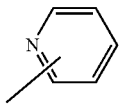

group.

The term pyrrole refers to a

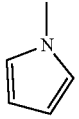

group or a

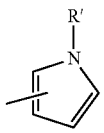

group, with R' as defined herein.

The term "morpholine" refers to a

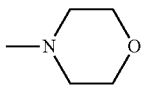

group, and encompasses also thiomorpholine.

The term "thiomorpholine" refers to a

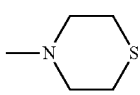

group.

The term "hexahydroazepine" refers to a

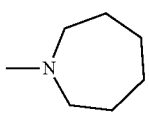

group.

The term "alkaryl" describes an alkyl, as defined herein, which is substituted by one or more aryl or heteroaryl groups, as defined herein. An example of alkaryl is benzyl.

The term "halide", "halogen" and "halo" describe fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)₂—R' end group or an —S(=O)₂— linking group, as these phrases are defined hereinabove, where R' is as defined herein.

The term "S-sulfonamide" describes a —S(=O)₂—NR'R" end group or a —S(=O)₂—NR'— linking group, as these phrases are defined hereinabove, with R' and R" as defined herein.

The term "N-sulfonamide" describes an R'S(=O)₂—NR"— end group or a —S(=O)₂—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "oxo" as used herein, describes a (=O) group, wherein an oxygen atom is linked by a double bond to the atom (e.g., carbon atom) at the indicated position.

The term "thiooxo" as used herein, describes a (=S) group, wherein a sulfur atom is linked by a double bond to the atom (e.g., carbon atom) at the indicated position.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The "hydroxyalkyl" is also referred to herein as "alcohol", and describes an alkyl, as defined herein, substituted by a hydroxy group.

The term "cyano" describes a —C≡N group.

The term "cyanurate" describes a

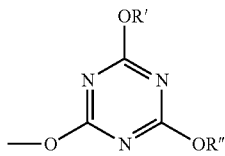

end group or

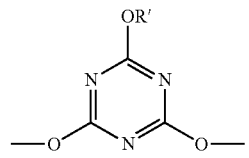

linking group, with R' and R" as defined herein.

The term "isocyanurate" describes a

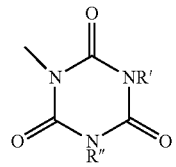

end group or

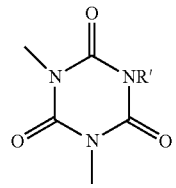

a linking group, with R' and R" as defined herein.

The term "thiocyanurate" describes a

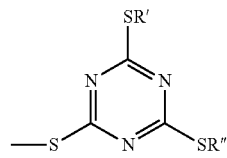

end group or

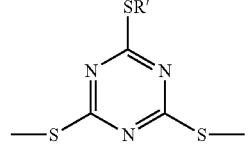

linking group, with R' and R" as defined herein.

The term "isocyanate" describes an —N=C=O group.

The term "isothiocyanate" describes an —N=C=S group.

The term "nitro" describes an —NO₂ group.

The term "acyl halide" describes a —(C=O)R"" group wherein R"" is halide, as defined hereinabove.

The term "azo" or "diazo" describes an —N=NR' end group or an —N=N— linking group, as these phrases are defined hereinabove, with R' as defined hereinabove.

The term "peroxo" describes an —O—OR' end group or an —O—O— linking group, as these phrases are defined hereinabove, with R' as defined hereinabove.

The term "carboxylate" as used herein encompasses C-carboxylate and O-carboxylate.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

A carboxylate can be linear or cyclic. When cyclic, R' and the carbon atom are linked together to form a ring, in C-carboxylate, and this group is also referred to as lactone. Alternatively, R' and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and O-thiocarboxylate.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

A thiocarboxylate can be linear or cyclic. When cyclic, R' and the carbon atom are linked together to form a ring, in C-thiocarboxylate, and this group is also referred to as thiolactone. Alternatively, R' and O are linked together to form a ring in O-thiocarboxylate. Cyclic thiocarboxylates can function as a linking group, for example, when an atom in the formed ring is linked to another group.

The term "carbamate" as used herein encompasses N-carbamate and O-carbamate.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

A carbamate can be linear or cyclic. When cyclic, R' and the carbon atom are linked together to form a ring, in O-carbamate. Alternatively, R' and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and O-thiocarbamate.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "amide" as used herein encompasses C-amide and N-amide.

The term "C-amide" describes a —C(=O)—NR'R" end group or a —C(=O)—NR'-linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

An amide can be linear or cyclic. When cyclic, R' and the carbon atom are linked together to form a ring, in C-amide, and this group is also referred to as lactam. Cyclic amides can function as a linking group, for example, when an atom in the formed ring is linked to another group.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R'" end group or a —R'NC(=N)— NW— linking group, as these phrases are defined hereinabove, where R', R" and R'" are as defined herein.

The term "hydrazine" describes a —NR'—NR"R'" end group or a —NR'—NR"-linking group, as these phrases are defined hereinabove, with R', R", and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

As used herein, the term "alkylene glycol" describes a —O—[(CR'R")$_z$—O]$_y$—R'" end group or a —O—[(CR'R")$_z$—O]$_y$— linking group, with R', R" and R'" being as defined herein, and with z being an integer of from 1 to 10, preferably, 2-6, more preferably 2 or 3, and y being an integer of 1 or more. Preferably R' and R" are both hydrogen. When z is 2 and y is 1, this group is ethylene glycol. When z is 3 and y is 1, this group is propylene glycol.

When y is greater than 4, the alkylene glycol is referred to herein as poly(alkylene glycol). In some embodiments of the present invention, a poly(alkylene glycol) group or moiety can have from 10 to 200 repeating alkylene glycol units, such that z is 10 to 200, preferably 10-100, more preferably 10-50.

The term "silyl" describes a —SiR'R"R'" end group or a —SiR'R"— linking group, as these phrases are defined hereinabove, whereby each of R', R" and R'" are as defined herein.

The term "siloxy" describes a —Si(OR')R"R'" end group or a —Si(OR')R"-linking group, as these phrases are defined hereinabove, whereby each of R', R" and R'" are as defined herein.

The term "silaza" describes a —Si(NR'R")R'" end group or a —Si(NR'R")— linking group, as these phrases are defined hereinabove, whereby each of R', R" and R'" is as defined herein.

The term "silicate" describes a —O—Si(OR')(OR")(OR'") end group or a —O—Si(OR')(OR")— linking group, as these phrases are defined hereinabove, with R', R" and R'" as defined herein.

As used herein, the term "epoxide" describes

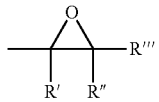

a end group or a

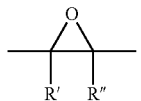

linking group, as these phrases are defined hereinabove, where R', R" and R'" are as defined herein.

As used herein, the term "methyleneamine" describes an —NR'—CH$_2$—CH=CR"R'" end group or a —NR'—CH$_2$—CH=CR"— linking group, as these phrases are defined hereinabove, where R', R" and R'" are as defined herein.

The term "phosphonate" describes a —P(=O)(OR')(OR") end group or a —P(=O)(OR')(O)— linking group, as these phrases are defined hereinabove, with R' and R" as defined herein.

The term "thiophosphonate" describes a —P(=S)(OR')(OR") end group or a —P(=S)(OR')(O)— linking group, as these phrases are defined hereinabove, with R' and R" as defined herein.

The term "phosphinyl" describes a —PR'R" end group or a —PR'— linking group, as these phrases are defined hereinabove, with R' and R" as defined hereinabove.

The term "phosphine oxide" describes a —P(=O)(R')(R") end group or a —P(=O)(R')— linking group, as these phrases are defined hereinabove, with R' and R" as defined herein.

The term "phosphine sulfide" describes a —P(=S)(R')(R") end group or a —P(=S)(R')— linking group, as these phrases are defined hereinabove, with R' and R" as defined herein.

The term "phosphite" describes an —O—PR'(=O)(OR") end group or an —O—PH(=O)(O)— linking group, as these phrases are defined hereinabove, with R' and R" as defined herein.

The term "carbonyl" or "carbonate" as used herein, describes a —C(=O)—R' end group or a —C(=O)— linking group, as these phrases are defined hereinabove, with R' as defined herein. This term encompasses ketones and aldehydes.

The term "thiocarbonyl" as used herein, describes a —C(=S)—R' end group or a —C(=S)— linking group, as these phrases are defined hereinabove, with R' as defined herein.

The term "oxime" describes a =N—OH end group or a =N—O— linking group, as these phrases are defined hereinabove.

The term "cyclic ring" encompasses a cycloalkyl, a heteroalicyclic, an aryl (an aromatic ring) and a heteroaryl (a heteroaromatic ring).

Other chemical groups are to be regarded according to the common definition thereof in the art and/or in line of the definitions provided herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Experimental Methods

Materials:

Pentane was washed with HNO$_3$/H$_2$SO$_4$ prior to distillation from Na/benzophenone/tetraglyme.

Toluene was refluxed over Na and distilled.

Dichloromethane was refluxed over CaH$_2$ and distilled.

N,N'-dimethylethylenediamine, N,N'-dibenzylethylenediamine, and NaCNBH$_3$ were purchased from Alfa Aesar and used as received.

2,2'-bipyrrolidine was purchased from Obiter and used as received. 2-pyridincarboxaldehyde was purchased from Arcos and used as received.

3,5-di-tert-butylsalicylaldehyde and triethylamine were purchased from Apollo and used as received.

ZnEt$_2$ solution, BnMgCl solution and anhydrous benzyl alcohol were purchased from Aldrich and used as received.

Mg(HMDS)$_2$ was synthesized following a procedure described in Mulvey, et. A1. *J. Am. Chem. Soc.* 1998, 120, 7816-7824.

2-(bromomethyl)-4,6-di-tert-butylphenol was synthesized following a procedure described in Appiah, et. al. *Inorg. Chem.* 2002, 41, 3656-3667.

L-lactide, D-lactide and rac-lactide lactides were purified by crystallization from dry toluene and sublimation.

ε-Caprolactone was purchased from Merck and was refluxed over CaH$_2$ and distilled prior to use.

Deuterated solvents were purchased from Cambridge Isotope Laboratories, Inc., degassed, and dried over activated 4 Å molecular sieves prior to use.

All reactions with air- and/or water sensitive compounds were carried out using standard Schlenk or glovebox techniques under dry N2 atmosphere.

Instrumental Analyses:

NMR spectra were recorded on a Bruker Avance 500 spectrometer at 25° C., unless otherwise stated. Chemical shifts ($\delta$) are listed as parts per million and coupling constants (J) in Hertz.

$^1$H NMR spectra are referenced using the residual solvent peak at $\delta$ =7.16 for $C_6D_6$, $\delta$=7.09, 7.00, 6.98, 2.09 for $C_7D_8$ and $\delta$=7.27 for $CDCl_3$.

$^{13}$C NMR spectra are referenced using the residual solvent peak at $\delta$=128.39 for $C_6D_6$ and $\delta$=77.23 for $CDCl_3$.

Diffusion NMR measurements were carried out on a Bruker Avance 500 equipped with a z-gradient system capable of producing a maximal pulse gradient of about 50 gauss cm$^{-1}$. These diffusion experiments were performed using a 5 mm inverse probe and DOSY pulse sequence. Sine-shaped pulse gradients of 4 ms duration were incremented from 0.7 to 32.2 gauss cm$^{-1}$ in 10 steps, and the pulse gradient separation was 50 ms. The diffusion coefficients were extracted from:

$$\ln\frac{I}{I_0} = -\gamma^2\delta^2G^2\left(\frac{2}{\pi}\right)^2\left(\frac{\Delta-\delta}{4}\right)^2 D = -bD$$

wherein I and $I_0$ are the echo intensity, in the presence and absence of the gradient pulse, respectively, $\gamma$ is the gyromagnetic ratio, G is the pulse gradient strength, $2/\pi$ is a geometrical correction factor due to the sine shape of the pulse gradients used, $\delta$ is the duration of the pulse gradient, $\Delta$ is the time interval between the leading edges of the pulse gradient used, and D is the diffusion coefficient. The diffusion coefficients were extracted from the slope of the plot of ln $I/I_0$ versus the b value. All diffusion NMR data were acquired at 298 K and were obtained in triplicate.

Molecular weights ($M_n$ and $M_w$) and molecular mass distributions ($M_w/M_n$) of PLA samples were measured by gel permeation chromatography (GPC) at 40° C., using THF as solvent, flow rate of eluent of 1 mL/minute, and narrow polystyrene standards as reference. The measurements were performed on a Jasco system equipped with an RI 1530 detector. A correction factor of 0.58 was employed for the molecular weight of PLA relative to polystyrene.

MS were obtained on either Waters XEVO-TQD or SYNAPT spectrometers.

Ionization methods: ESI (positive or negative). The enantiomeric excess of the unconsumed lactide was determined by chiral GC using HP5890 series II system equipped with RESTEK Rt-bDEXm column.

X-ray diffraction measurements were performed on an ApexDuo (Bruker-AXS) diffractometer system, using Mo K$\alpha$ ($\lambda$, =0.7107 Å) radiation. The analyzed crystals were embedded within a drop of viscous oil and freeze-cooled to ca. 110 K.

Elemental analyses were performed in the micro-analytical laboratory at the Hebrew University of Jerusalem.

Example 1

Ligand Syntheses

The structures of exemplary {ONNN}—H ligand precursors according to some embodiments of the present invention are presented in FIG. 1. These exemplary ligands include the two enantiomers of the bipyrrolidine based ligand ((R,R)- or (S,S)-Lig$^1$H) and their non-chiral varieties bearing the diaminoethane bridge having either two N-methyl (Lig$^2$H) or two N-benzyl (Lig$^3$H) substituents.

The ligand precursors were prepared readily in high yields by condensation of the diamines with pyridine carboxaldehyde and reduction, followed by a substitution reaction with the bromomethyl-derivative of the phenol.

Synthesis of (S,S)—N-(2-pyridylmethyl)-2,2'-bipyrrolidine

This compound was synthesized by modification of a procedure described in Chiang et al. 2014 (supra). To a solution of (S,S)-2,2'-bipyrrolidine (0.45 gram, 3.2 mmol) in methanol (10 mL) was added drop-wise a solution of 2-pyridinecarboxaldehyde (0.35 gram, 3.2 mmol) in methanol (5 mL). The reaction mixture was stirred at room temperature for 1 hour forming an orange solution. NaCNBH$_3$ (0.82 gram, 13.0 mmol) was added followed by addition of trifluoroacetic acid (2 mL), and the solution was stirred for additional 3 hours. After neutralization with NaOH 4M solution, the crude product was extracted with 3 portions of dichloromethane (30 mL). The collected organic layer was dried over Na$_2$SO$_4$ and solvent was removed under vacuum yielding a yellow oil in 92% yield $^1$H NMR (CDCl$_3$, 500 MHz): $\delta$ 8.53 (d, 1H, J=4.51 Hz, ArH), 7.64 (td, 1H, J=7.67 Hz, J=1.53 Hz, ArH), 7.43 (d, 1H, J=7.69 Hz, ArH), 7.14 (dd, 1H, J=7.60 Hz, J=5.16 Hz, ArH), 4.33 (d, 1H, J=14.17 Hz, CH$_2$), 3.63 (d, 1H, J=14.20 Hz, CH$_2$), 3.06 (q, 1H, J=7.62 Hz, CH), 3.00-2.96 (m, 2H, CH$_2$), 2.86-2.80 (m, 1H, CH$_2$), 2.76-2.72 (m, 1H, CH$_2$), 2.37 (q, 1H, J=7.70 Hz, CH), 2.01-1.89 (m, 1H, CH$_2$), 1.85-1.68 (m, 6H, CH$_2$), 1.61-1.54 (m, 1H, CH$_2$), 1.44-1.38 (m, 1H, CH$_2$).

$^{13}$C NMR (CDCl$_3$, 125 MHz): $\delta$ 160.69 (C), 149.22 (CH), 136.50 (CH), 122.91 (CH), 121.87 (CH), 68.25 (CH), 64.11 (CH), 62.76 (CH$_2$), 55.26 (CH$_2$), 46.71 (CH$_2$), 28.47 (CH$_2$), 28.39 (CH$_2$), 25.07 (CH$_2$), 24.06 (CH$_2$).

MS (ESI): Calc for C$_{14}$H$_{21}$N$_3$O: 231.3, found: 232.3.

Synthesis of (S,S)-Lig$^1$H (see, FIG. 1)

(S,S)-Lig$^1$H (2,4-di-tert-butyl-6-(((2S,2'S)-1'-(pyridin-2-ylmethyl)-[2,2'-bipyrrolidin]-1-yl)methyl)phenol) was synthesized from (S,S)—N-(2-pyridylmethyl)-2,2'-bipyrrolidine and 2-(bromomethyl)-4,6-di-tert-butylphenol according to the procedure described in Chiang et al., 2014 (supra).

Synthesis of (R,R)-Lig$^1$H (see, FIG. 1)

(R,R)-Lig$^1$H 2,4-di-tert-butyl-6-(((2R,2'R)-1'-(pyridin-2-ylmethyl)-[2,2'-bipyrrolidin]-1-yl)methyl)phenol was synthesized according to procedure described herein for (S,S)-Lig$^1$H employing (R,R)-2,2'-bipyrrolidine.

Synthesis of N,N'-dimethyl-N-(2-pyridylmethyl)-ethylenediamine

To a solution of N,N'-dimethylethylenediamine (1.61 gram, 18.26 mmol) in methanol (20 mL) was added drop-wise a solution of 2-pyridinecarboxaldehyde (1.96 gram, 18.29 mmol) in methanol (10 mL). The reaction mixture was stirred at room temperature for 1 hour forming an orange solution. NaCNBH$_3$ (3.5 grams, 55.7 mmol) was added followed by addition of trifluoroacetic acid (5 mL), and the solution was stirred for additional 3 hours. After neutralization with NaOH 4M solution, the crude product was extracted with 3 portions of dichloromethane (30 mL). The collected organic layer was dried over Na$_2$SO$_4$ and solvent was removed under vacuum yielding a yellow oil in 95% yield.

$^1$H NMR (CDCl$_3$, 500 MHz): δ 8.54 (ddd, 1H, J=4.85 Hz, J=1.85 Hz, J=0.85 Hz, ArH), 7.65 (td, 1H, J=7.65 Hz, J=1.82 Hz, ArH), 7.40 (d, 1H, J=7.84 Hz, ArH), 7.16 (ddd, 1H, J=7.65 Hz, J=4.80 Hz, J=1.0 Hz, ArH), 3.67 (s, 2H, Ar—CH$_2$), 2.70 (t, 2H, J=6.25 Hz, CH$_2$), 2.60 (t, 2H, J=6.16 Hz, CH$_2$), 2.42 (s, 3H, CH$_3$), 2.28 (s, 3H, CH$_3$).

$^{13}$C NMR (CDCl$_3$, 125 MHz): δ 159.61 (C), 149.25 (CH), 136.60 (CH), 123.13 (CH), 122.14 (CH), 64.26 (CH$_2$), 56.97 (CH$_2$), 49.44 (CH$_2$), 42.81 (CH$_3$), 36.50 (CH$_3$).

MS (ESI): Calc for C$_{10}$H$_{17}$N$_3$: 179.3, found: 180.3 (MH$^+$).

Synthesis of Lig$^2$H (see, FIG. 1)

A solution of 2-(bromomethyl)-4,6-di-tert-butylphenol (2.1 grams, 7.02 mmol) in THF (10 mL) was added dropwise to a solution of N,N'-dimethyl-N-(2-pyridylmethyl)-ethylenediamine (1.2 gram, 6.69 mmol) and triethylamine (1.5 mL) in THF (20 mL) and stirred for 2 hours. The solid that had formed was filtered out, and the solvent was removed under vacuum. The crude product was purified by passing through a plug of neutral alumina with dichloromethane, followed by flash-chromatography on silica gel (eluent 20:1 CH$_2$Cl$_2$/MeOH) to afford a pale yellow oil in an overall yield of 65%.

$^1$H NMR (CDCl$_3$, 500 MHz): δ 8.52 (ddd, 1H, J=4.93 Hz, J=1.82 Hz, J=0.87 Hz, ArH), 7.63 (td, 1H, J=7.60 Hz, J=1.80 Hz, ArH), 7.56 (d, 1H, J=7.80 Hz, ArH), 7.19 (d, 1H, J=2.41 Hz, ArH), 7.14 (ddd, 1H, J=7.44 Hz, J=4.88 Hz, 1.09 Hz, ArH), 6.81 (d, 1H, J=2.43 Hz, ArH), 3.67 (brs, 4H, CH$_2$), 2.64 (brs, 4H, CH$_2$), 2.26 (s, 3H, CH$_3$), 2.23. (s, 3H, CH$_3$), 1.41 (s, 9H, C(CH$_3$)$_3$), 1.28 (s, 9H, C(CH$_3$)$_3$).

$^{13}$C NMR (CDCl$_3$, 125 MHz): δ 159.59 (C), 154.48 (C), 149.05 (CH), 140.39 (C), 136.64 (CH), 135.56 (C), 123.47 (CH), 123.38 (CH), 122.11 (CH), 121.49 (C), 64.62 (CH$_2$), 62.20 (CH$_2$), 55.28 (CH$_2$), 54.43 (CH$_2$), 42.59 (CH$_3$), 41.71 (CH$_3$), 34.99 (C), 34.25 (C), 31.85 (CCH$_3$), 29.73 (CCH$_3$).

HRMS (ESI): Calc for C$_{25}$H$_{39}$N$_3$O: 397.3093, found: 398.3165 (MH$^+$).

Synthesis of N,N'-dibenzyl-N-(2-pyridylmethyl)-ethylenediamine

This compound was synthesized in an analogous manner to the procedure described above for N,N'-dimethyl-N-(2-pyridylmethyl)-ethylenediamine, starting from N,N'-dibenzyl-ethylenediamine. The product was obtained as a yellow oil in an overall yield of 92%.

$^1$H NMR (CDCl$_3$, 500 MHz): δ 8.48 (d, 1H, J=4.90 Hz, ArH), 7.62 (td, 1H, J=7.70 Hz, J=1.75 Hz, ArH), 7.42 (d, 1H, J=7.70 Hz, ArH), 7.33-7.22 (m, 10H, ArH), 7.13 (t, 1H, J=4.92 Hz, ArH), 3.74 (s, 2H, CH$_2$), 3.65 (s, 2H, CH$_2$), 3.64 (s, 2H, CH$_2$), 2.73 (t, 2H, J=5.80 Hz, CH$_2$), 2.71 (t, 2H, J=5.80 Hz, CH$_2$).

$^{13}$C NMR (CDCl$_3$, 125 MHz): δ 160.18 (C), 149.03 (CH), 139.31 (C), 136.54 (CH), 129.03 (CH), 128.90 (C), 128.47 (CH), 128.43 (CH), 128.22 (CH), 127.17 (CH), 127.01 (CH), 122.99 (CH), 122.06 (CH), 60.54 (CH$_2$), 59.25 (CH$_2$), 53.79 (CH$_2$), 53.75 (CH$_2$), 46.76 (CH$_2$).

MS (ESI): Calc for C$_{22}$H$_{25}$N$_3$: 331.2, found: 332.4 (MH$^+$).

Synthesis of Lig$^3$H (see, FIG. 1)

A solution of 2-(bromomethyl)-4,6-di-tert-butylphenol (1.2 gram, 4.01 mmol) in THF (10 mL) was added dropwise to a solution of N,N'-dibenzyl-N-(2-pyridylmethyl)-ethylenediamine (1.31 gram, 3.95 mmol) and triethylamine (0.75 mL) in THF (20 mL) and stirred for 2 hours. The solid that had formed was filtered out, and the solvent was removed under vacuum. The crude product was purified by flash-chromatography on silica gel (eluent 20:1 CH$_2$Cl$_2$/MeOH) to afford a pale yellow oil in an overall yield of 68%.

$^1$H NMR (CDCl$_3$, 500 MHz): δ 10.90 (brs, 1H, OH), 8.47 (ddd, 1H, J=4.90 Hz, J=1.84 Hz, 0.88 Hz, ArH), 7.66 (d, 1H, J=7.99 Hz, ArH), 7.58 (td, 1H, J=7.64 Hz, 1.84 Hz, ArH), 7.35 (d, 2H, J=7.02 Hz, ArH), 7.27-7.16 (m, 9H, ArH), 7.11 (ttt, 1H, J=7.44 Hz, 4.92 Hz, 1.06 Hz, ArH), 6.81 (d, 1H, J=2.35 Hz, ArH). 3.63 (brs, 2H, CH$_2$), 3.59 (s, 2H, CH$_2$), 3.48 (s, 2H, CH$_2$), 3.45 (brs, 2H, CH$_2$), 2.6 (brs, 4H, CH$_2$), 1.49 (s, 9H, C(CH$_3$)), 1.28 (s, 9H, C(CH$_3$)).

$^{13}$C NMR (CDCl$_3$, 125 MHz): δ 159.92 (C), 154.06 (C), 148.83 (CH), 140.54 (C), 138.84 (C), 137.22 (C), 136.55 (CH), 135.67 (C), 129.84 (CH), 129.28 (CH), 128.40 (CH), 128.35 (CH), 127.46 (CH), 127.10 (CH), 123.91 (CH), 123.45 (CH), 122.96 (CH), 122.02 (CH), 121.52 (C), 60.41 (CH$_2$), 58.92 (CH$_2$), 58.30 (CH$_2$), 57.77 (CH$_2$), 50.83 (CH$_2$), 50.25 (CH$_2$), 35.06 (C), 34.28 (C), 31.85 (CH$_3$), 29.75 (CH$_3$).

HRMS (ESI): Calc for C$_{37}$H$_{47}$N$_3$O: 549.3719, found: 550.3791 (MH$^+$).

Syntheses of Lig$^{4-7}$H (see, FIG. 1)

Lig$^{4-7}$H were prepared similarly to Lig$^1$H, using respective starting materials.

Example 2

Syntheses of the Zinc Complexes

Reacting the ligand precursors Lig$^{1-3}$H with diethylzinc, as depicted in Scheme 3 below with reference to Lig$^1$H, gave the corresponding Lig$^{1-3}$Zn-Et in high to quantitative yields.

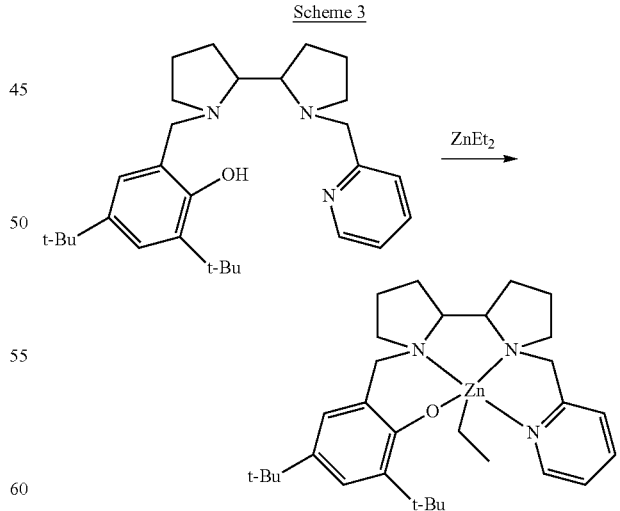

Scheme 3

$^1$H NMR and mass-spectroscopic analyses supported the formation of mononuclear complexes as single stereoisomers. This stands in sharp contrast with a previously described zinc system that was found to be bridging dinuclear in solution. The formation of single diastereomers of (R,R)- and (S,S)-Lig$^1$Zn-Et stands in contrast to the zinc complexes of the chiral tridentate ligands previously described, which were formed as less-defined diastereomer mixtures.

The complex Lig$^1$Zn-Et was found to form as a rigid complex, while Lig$^2$Zn-Et and Lig$^3$Zn-Et appeared fluxional according to broad absorptions in the $^1$H NMR spectrum at RT, which sharpened upon cooling.

To gain further structural insight, crystallization attempts of the three zinc complexes dissolved in dichloromethane at −35° C. were made. Single crystals suitable for X-ray diffraction measurements were obtained for all complexes. The crystallographic structures of Lig$^1$Zn—Cl and Lig$^2$Zn-Et and Lig$^3$Zn-Et are shown in FIGS. 2A-C.

As shown in FIGS. 2A-C, the structures of complexes Lig$^2$Zn-Et and Lig$^3$Zn-Et were consistent with their proposed constitution, however a chloro complex was obtained for the bipyrrolidine-based ligand—Lig$^1$Zn—Cl instead of Lig$^1$Zn-Et, possibly due to more facile crystallization of the Lig$^1$Zn—Cl impurity formed by reaction of Lig$^1$Zn-Et with traces of HCl in the solvent.

As further shown in FIGS. 2A-C, all structures feature a pentacoordinate mononuclear zinc complex in which all donors of the {ONNN} ligands are bound to the zinc center. The geometry around the zinc is intermediate between square-pyramidal and trigonal-bipyramidal for Lig$^1$Zn—Cl and Lig$^2$Zn-Et ($\tau$=0.40, 0.34, respectively, see, for example, Addison et al., *J. Chem. Soc.* Dalton Trans. 1984, 1349-1356), and almost pure square-pyramidal for Lig$^3$Zn-Et ($\tau$=0.16) with the ethyl group at the apical position.

The bond lengths of the {ONNN} donors to the zinc are unexceptional, however the bipyrrolidine-based Lig$^1$ binds more tightly. The two internal N-donors become stereogenic upon binding to the zinc. For the chiral Lig$^1$ the two N-donors were found to have the same relative configurations [see, Chiang et al., 2-14 (supra); Sergeeva, et al. *Chem. Commun.* 2009, 3053-3055; Sergeeva et al. *Eur. J. Inorg. Chem.* 2013, 3362-3369; Miller et al. *Eur. J. Inorg. Chem.* 2014, 1485-1491; Jones et al. *Chem. Commun.* 2014, 50, 15967-15970; and Press et al. *Angew. Chem. Int. Ed.* 2015, 54, 14858-14861], substantiating their ability to induce a predetermined 'chirality-at-metal'. Notably, the two non-chiral ligands Lig$^2$ and Lig$^3$ were found to wrap around the zinc such that the stereogenic N-donors have opposite configurations. This may explain their fluxional character.

Synthesis of Lig$^1$Zn-Et

To a stirred solution of (S,S)-Lig$^1$H (106 mg, 0.24 mmol) in toluene (2 mL), was added a solution of ZnEt$_2$ (0.36 mL, 0.24 mmol, 1M hexanes solution) drop-wise. The resulting mixture was stirred at room temperature for 2 hours and thereafter the solvent was removed under vacuum. The residue was washed with pentane yielding a white solid in 91% yield. The enantiomeric complex (R,R)-Lig$^1$Zn-Et was prepared accordingly employing (R,R)-Lig$^1$H. X-ray quality crystals of (R,R)-Lig$^1$Zn—Cl were grown from dichloromethane.

$^1$H NMR (C$_6$D$_6$, 500 MHz): δ 8.94 (d, 1H, J=3.78 Hz, ArH), 7.64 (d, 1H, J=2.46 Hz, ArH), 7.01 (t, 1H, J=7.59 Hz, ArH), 6.97 (d, 1H, J=1.83 Hz, ArH), 6.67 (m, 2H, ArH), 3.78 (d, 1H, J=11.25, CH$_2$), 3.40 (brs, 1H, CH), 3.38 (d, 1H, J=6.21 Hz, CH$_2$), 3.06 (d, 1H, J=14.38 Hz, CH$_2$), 2.89-2.84 (m, 1H, CH$_2$), 2.59-2.47 (m, 3H, CH$_2$), 2.25-2.19 (m, 2H, CH$_2$), 1.93 (s, 9H, C(CH$_3$)$_3$), 1.50 (s, 9H, C(CH$_3$)$_3$), 1.45-1.33 (m, 6H, CH$_2$), 1.24-1.17 (m, 2H, CH$_2$), 0.96-0.87 (m, 3H, CH$_3$), 0.44-0.37 (m, 1H, CH$_2$), 0.18-0.11 (m, 1H, CH$_2$).

$^{13}$C NMR (C$_6$D$_6$, 125 MHz): δ 166.17 (C), 155.31 (C), 149.53 (CH), 137.85 (C), 136.49 (CH), 133.21 (C), 125.95 (CH), 124.00 (CH), 123.30 (C), 122.75 (CH), 122.12 (CH), 69.53 (CH$_2$), 63.46 (CH$_2$), 62.25 (CH$_2$), 59.46 (CH$_2$), 54.23 (CH$_2$), 50.15 (CH$_2$), 35.97 (C), 34.15 (C), 32.51 (CH$_3$), 30.54 (CH$_3$), 26.82 (CH$_2$), 25.65 (CH$_2$), 22.80 (CH$_2$), 22.71 (CH$_3$), 19.81 (CH$_2$), −0.89 (CH$_2$).

Crystal Data for Complex [(R,R)-Lig$^1$Zn—Cl]. C$_{29}$H$_{42}$ClN$_3$OZn, CH$_2$Cl$_2$; M=634.40; orthorhombic; space group P 2$_1$ 2$_1$ 2$_1$; a=7.9463(5) Å, b=17.5296(12) Å, c=22.3259(15)Å, V=3109.9(4) Å3; T=110(2) K; Z=2; Dc=1.355 g cm-3; μ (Mo Kα)=1.075 mm-1; R1=0.0834 and wR2=0.1647 or 5003 reflections with I>2σ (I); R1=0.0627 and wR2=0.1525 for all 4050 unique reflections. See, FIG. 2A

Synthesis of Lig$^2$Zn-Et

To a stirred solution of Lig$^2$H (143 mg, 0.36 mmol) in toluene (2 mL), was added a solution of ZnEt$_2$ (0.36 mL, 0.36 mmol, 1M hexanes solution) drop-wise. The resulting mixture was stirred at room temperature for 2 hours after which the solvent was removed under vacuum, resulting in a pale yellow solid quantitatively. X-ray quality crystals of Lig$^1$Zn-Et were grown from toluene/pentane mixture at −35° C.

$^1$H NMR (C$_6$D$_6$, 500 MHz): δ 8.75 (d, 1H, J=4.07 Hz, ArH), 7.64 (d, 1H, J=2.60 Hz, ArH), 7.06 (brs, 2H, ArH), 6.91 (brs, 1H, ArH), 6.66 (t, 1H, J=6.08 Hz, ArH), 3.94 (brs, 1H, CH$_2$), 3.77 (brs, 2H, CH$_2$), 2.96 (brs, 2H, CH$_2$), 2.61 (brs, 3H, CH$_2$), 2.07 (s, 6H, CH$_3$), 1.82 (s, 9H, C(CH$_3$)$_3$), 1.52 (s, 9H, C(CH$_3$)$_3$), 1.47 (t, 3H, J=8.20 Hz, CH$_3$), 0.41-0.33 (m, 1H, CH$_2$), 0.28-0.21 (m, 1H, CH$_2$).

$^{13}$C NMR (C$_6$D$_6$, 125 MHz): δ 165.32 (C), 155.14 (C), 149.52 (CH), 137.96 (C), 136.95 (C), 133.89 (C), 125.51 (C), 123.86 (CH), 123.14 (CH), 122.86 (CH), 63.78 (CH$_2$), 55.43 (CH$_2$), 44.39 (CH$_2$), 42.18 (CH$_2$), 35.77 (CC)), 34.23 (C), 32.51 (CCH$_3$), 30.33 (CCH$_3$), 14.52 (CH$_3$), −2.14 (CH$_2$).

Crystal Data for Complex [Lig$^2$Zn-Et]. C$_{27}$H$_{43}$N$_3$OZn; M=516.86; monoclinic; space group C 2/c; a=18.9185(16) Å, b=16.0073(15) Å, c=17.7938(16)Å, β=98.251(4)°, V=5332.8 (8) Å3; T=110(2) K; Z=8; Dc=1.288 g cm-3; μ (Mo Kα)=0.435 mm-1; R1=0.0480 and wR2=0.1355 for 6635 reflections with I>2σ (I); R1=0.0396 and wR2=0.1291 for all 5626 unique reflections. See, FIG. 2B

Synthesis of Lig$^3$Zn-Et

To a stirred solution of Lig$^3$H (130 mg, 0.24 mmol) in toluene (2 mL), was added a solution of ZnEt$_2$ (0.24 mL, 0.24 mmol, 1M hexanes solution) drop-wise. The resulting mixture was stirred at room temperature for 2 hours after which the solvent was removed under vacuum, resulting in white solid quantitatively. X-ray quality crystals of Lig$^1$Zn-Et were grown from pentane at −35° C.

$^1$H NMR (C$_6$D$_6$, 500 MHz): δ 8.97 (d, 1H, J=3.86 Hz, ArH), 7.71 (d, 1H, J=2.46 Hz, ArH), 7.36 (d, 2H, J=7.10 Hz, ArH), 7.28 (t, 2H, J=7.49 Hz, ArH), 7.21-7.15 (m, 5H, ArH), 7.05 (t, 1H, J=7.41 Hz, 1H), 6.95-6.92 (m, 2H, ArH), 6.70 (t, 1H, J=6.35 Hz, ArH), 6.66 (d, 1H, ArH, 7.65 Hz), 4.14 (br, 1H, CH$_2$), 3.91 (br, 2H, CH$_2$), 3.75-3.59 (m, 3H, CH$_2$), 3.46(br, 1H, CH$_2$), 3.14 (br, 1H, CH$_2$), 2.99 (br, 1H, CH$_2$), 2.55 (br, 1H, CH$_2$), 2.35 (br, 1H, CH$_2$), 2.11 (br, 1H, CH$_2$), 1.91 (s, 9H, C(CH$_3$)$_3$), 1.77 (t, 3H, J=6.8 Hz, CH$_3$), 1.57 (s, 9H, C(CH$_3$)$_3$), 0.69 (br, 1H, CH$_2$), 0.59 (br, 1H, CH$_2$).

$^{13}$C NMR (C$_6$D$_6$, 125 MHz): δ 165.65 (C), 155.25 (CH), 149.91 (CH), 138.04 (C), 137.87 (C), 137.35 (C), 134.50 (C), 133.54 (C), 132.97 (C), 132.08 (CH), 131.63 (CH), 129.31 (CH), 128.54 (CH), 128.50 (CH), 126.47 (CH), 125.67 (CH), 123.68 (CH), 122.97 (CH), 122.18 (CH), 57.98 (CH$_2$), 57.78 (CH$_2$), 56.23 (CH$_2$), 54.05 (CH$_2$), 50.20 (CH$_2$), 48.78 (CH$_2$), 35.82 (C), 34.25 (C), 32.49 (CH$_3$), 30.32 (CH$_3$), 14.88 (CH$_3$), −0.63 (CH$_2$).

Crystal Data for Complex [Lig$^3$Zn-Et]. C$_{39}$H$_{51}$N$_3$OZn; M=643.19; triclinic; space group P −1; a=11.0091(15) Å, b=12.5903(14) Å, c=15.051(2)Å, α=65.937(4)°, β=73.908(5)°, γ=65.779(4)°, V=1722.2(4) Å3; T=110(2) K; Z=2; Dc=1.240 g cm-3; μ (Mo Kα)=0.747 mm-1; R1=0.0476 and wR2=0.1073 for 6084 reflections with I>2σ (I); R1=0.0408 and wR2=0.1035 for all 5440 unique reflections. See, FIG. 2C Complexes Lig$^{4-7}$Zn-Et were similarly prepared with the respective ligands.

In Situ Generation of Zinc-OBn complexes:

General Procedure:

0.02 mmol of zinc ethyl complex and benzyl alcohol (2 equivalents) were dissolved in 0.50 mL of toluene-d$_8$ in an NMR tube inside the glove box. The mixture was shaken and analyzed by $^1$H NMR spectroscopy at room temperature. After the required time the corresponding benzyloxy complex was obtained in quantitative yield. The stability of the benzyloxy complexes with excess of benzyl alcohol was confirmed up to 343K for 24 hours, with no indication of ligand detachment.

Lig$^1$Zn-OBn: Full conversion within several seconds.

$^1$H NMR (C$_6$D$_6$, 500 MHz): δ 8.75 (brs, 1H, ArH), 7.59 (d, 1H, J=2.46 Hz, ArH), 7.14-7.12 (m, 4H, ArH), 7.08-7.05 (m, 2H, ArH), 6.94 (d, 1H, J=2.44 Hz, ArH), 6.87 (t, 1H, J=5.82 Hz, ArH), 6.31 (d, 1H, J=7.75 Hz, ArH), 4.21 (d, 1H, J=14.72 Hz, CH$_2$), 3.96 (brs, 3H, CH$_2$). 3.84 (d, 1H, J=10.76 Hz, CH$_2$), 3.59-3.54 (m, 1H, CH$_2$), 3.40 (d, 1H, J=10.78 Hz, CH$_2$), 2.98-2.95 (m, 1H, CH$_2$), 2.91 (d, 2H, J=15.05 Hz, CH$_2$), 2.85-2.81 (m, 1H, CH$_2$), 2.47-2.44 (m, 1H, CH$_2$), 2.36-2.27 (m, 1H, CH$_2$), 1.76 (s, 9H, C(CH$_3$)$_3$), 1.66-1.60 (m, 3H, CH$_2$), 1.45 (s, 9H, C(CH$_3$)$_3$), 1.10-1.05 (m, 2H, CH$_2$), 0.95-0.85 (m, 2H, CH$_2$).

Lig$^2$Zn-OBn: Full conversion within 1 hour.

$^1$H NMR (C$_6$D$_6$, 500 MHz): δ 8.69 (brs, 1H, ArH), 8.41 (brs, 1H, ArH), 7.61(brs, 1H, ArH), 7.56 (brs, 1H, ArH), 7.07-6.95 (m, 3H, ArH), 6.81 (brs, 1H, ArH), 6.51 (brs, 1H, ArH), 6.23 (brs, 1H, ArH), 6.09 (brs, 1H, ArH), 4.21 (d, 1H, J=14.20 Hz, CH$_2$), 4.12 (d, 1H, J=11.09 Hz, CH$_2$), 3.97 (d, 1H, J=11.09 Hz, CH$_2$), 3.31 (d, 1H, J=14.26 Hz, CH$_2$), 3.05 (brs, 1H, CH$_2$), 2.91 (brs, 1H, CH$_2$), 2.74-2.61 (m, 4H, CH$_2$), 2.31 (brs, 3H, CH$_3$), 2.07 (brs, 3H, CH$_3$), 1.72 (s, 9H, C(CH$_3$)$_3$), 1.47 (s, 9H, C(CH$_3$)$_3$).

Lig$^3$Zn-OBn: Full conversion within 2 hours.

$^1$H NMR (C$_6$D$_6$, 500 MHz): δ 8.72 (brs, 1H, ArH), 7.66 (brs, 1H, ArH), 7.50-7.47 (m, 2H, ArH), 7.04-6.97 (m, 14H, ArH), 6.79 (brs, 1H, ArH), 6.44 (brs, 1H, ArH), 6.21 (brs, 1H, ArH), 4.47 (brs, 1H, CH$_2$), 4.20 (brs, 1H, CH$_2$), 4.10 (brs, 2H, CH$_2$), 3.87 (brs, 2H, CH$_2$), 3.44 (brs, 2H, CH$_2$), 3.05 (brs, 2H, CH$_2$), 2.41 (brs, 2H, CH$_2$), 1.83 (s, 9H, C(CH$_3$)$_3$), 1.48 (s, 9H, C(CH$_3$)$_3$).

Example 3

Polymerization Catalysis by Zinc Complexes

General Polymerization Procedure:

To a solution of a catalyst (0.01 mmol) in dichloromethane (5 mL), benzyl alcohol (0.01 mmol) was added, and the reaction mixture was stirred at room temperature for 10 minutes. Then, a lactide (e.g., rac-lactide; 432 mg, 3 mmol) was added, and the reaction was stirred at room temperature. The reaction was terminated by the addition of methanol (1 mL) and the volatiles were removed under vacuum. The tacticity of the PLA samples was determined by the homonuclear-decoupled $^1$H NMR spectrometry (500 MHz, CDCl$_3$) as previously described [see, for example, Stopper et al. Macromolecules 2012, 45, 698-704; and Chen et al. Macromolecules 2006, 39, 3745-3752].

General Procedure for Kinetic Studies:

0.25 μmol of zinc ethyl complex and a lactide (e.g., rac-lactide; 100 equivalents) were dissolved in 0.50 mL of dichloromethane-d$_2$ in an NMR test tube inside the glove box. Benzyl alcohol (1 equivalent) was spread over the tube cap. Before placing in an NMR spectrometer, the tube was shaken in order to generate the benzyloxy complex. The polymerization rate was evaluated by comparing the integration of the methine peaks of the monomer and the formed polymer to the residual signal of the solvent in the $^1$H NMR spectra, as described hereinabove.

Reactivity:

Reacting the exemplary complexes described in Example 2 hereinabove with benzyl alcohol led to a fast exchange of the ethyl group with a benzyloxy group. The zinc complex Lig$^1$Zn-Et led to Lig$^1$Zn-OBn within seconds whereas the complexes Lig$^{2,3}$Zn-Et led to the corresponding Lig$^{2,3}$Zn-OBn more slowly, and for Lig$^3$Zn-Et full conversion was reached after 2 hours. No evidence was found for decomposition of the {ONNN} ligand from the zinc in any of these reactions, supporting the stability of these complexes. This stands in sharp contrast with the inertness of Zn-Et bond in the chiral {ONN}-Zn-Et complexes previously described.

The $^1$H NMR spectrum of [Lig$^1$ZnOBn] indicates that it is a single rigid diastereoisomer. The $^1$H NMR spectra of [Lig$^2$ZnOBn] and [Lig$^3$ZnOBn] feature broader peaks that are consistent with fluxional stereoisomers.

The diffusion coefficients of the benzyloxy complexes, elucidated from $^1$H DOSY experiments, are slightly lower than the diffusion coefficients of the ethyl complexes, as shown in Table 1 below, consistent with the bulkier labile group. This suggests that the benzyloxy complexes are monomeric in solution.

TABLE 1

| Initiator | Lig$^1$Zn | Lig$^2$Zn | Lig$^3$Zn |
|---|---|---|---|
| —Et | 6.793 | 7.543 | 6.561 |
| —OBn | 6.240 | 6.492 | 5.856 |

Polymerization of racemic lactide:

Polymerization reactions were run in dichloromethane, at room temperature, by adding benzyl alcohol to the zinc-ethyl complexes in the presence of rac-lactide.

Table 2 below presents the data obtained for polymerization of rac-lactide in DCM at room temperature.

TABLE 2

| Entry | Initiator | [I]:[LA]:[BnOH] | Time | Conv. | $M_{n\ (calc)}$ (g/mol$^{-1}$) | $M_n$ (g/mol$^{-1}$) | $M_w/M_n$ | Pm |
|---|---|---|---|---|---|---|---|---|
| 1. | Lig$^1$ZnEt | 1:300:1 | 15 min | >0.95 | 43200 | 44800 | 1.10 | 0.70 |
| 2. | Lig$^1$ZnEt | 1:300:2 | 10 min | >0.95 | 21600 | 21000 | 1.08 | 0.71 |
| 3. | Lig$^1$ZnEt | 1:300:4 | 10 min | >0.95 | 10800 | 11200 | 1.09 | 0.71 |
| 4. | Lig$^2$ZnEt | 1:300:1 | 2 h | 0.90 | 38900 | 35400 | 1.09 | 0.69 |
| 5. | Lig$^2$ZnEt | 1:300:2 | 2 h | 0.91 | 21600 | 19600 | 1.11 | 0.70 |
| 6. | Lig$^2$ZnEt | 1:300:4 | 2 h | 0.91 | 9800 | 11200 | 1.13 | 0.70 |
| 7. | Lig$^3$ZnEt | 1:300:1 | 2 h | 0.66 | 28500 | 22400 | 1.12 | 0.80 |
| 8. | Lig$^3$ZnEt | 1:300:2 | 2 h | 0.70 | 15000 | 13600 | 1.15 | 0.81 |

Preliminary polymerization runs of 300 equivalents employing Lig$^1$Zn-Et/BnOH for two hours revealed that the monomer was fully consumed. The polymerization time was therefore reduced to 15 minutes, after which more than 95% of the monomer was consumed (see, Table 1, entry 1). This represents one of the highest activities reported for zinc complexes.

The molecular weight distributions of the polymer samples were very narrow, with PDI (polydispersity index) values of $M_w/M_n$<1.10 in certain cases, and PLA molecular weight in concert with the monomer/initiator molar ratio support a living system and a fast and full activation of the pre-catalyst.

Increasing the benzyl alcohol ratio to beyond a single equivalent led to "immortal polymerization", namely, the formation of more than a single chain for every zinc center mediated by chain transfer (see, Table 1, entries 2, 3). The polymer samples produced under the "immortal" conditions also feature very narrow Mw/Mn values, and molecular weights consistent with the theoretical values, supporting a well behaved catalytic species.

Complexes of Lig$^2$Zn-Et and Lig$^3$Zn-Et were also found active for rac-LA polymerization upon activation with benzyl alcohol, whereby reaction times of about 2 hours were required to reach high conversion. Narrow PDI's and "immortal" behavior were noted also for these catalysts (see, Table 1, entries 4-8).

$^1$H NMR spectroscopic monitoring the consumption of rac-LA by each [LigZnEt] complex in the presence benzyl alcohol in CD$_2$Cl$_2$ at room temperature revealed that, after an incubation period, first-order kinetics are established (see, for example FIGS. 3A and 3B). The incubation period is attributed to the exchange of the ethyl group by the benzyloxy group, and, consistently with the measurements above, is hardly noticeable for [Lig$^1$ZnEt], on the order of several minutes for [Lig$^2$ZnEt], and 30 minutes for [Lig$^3$ZnEt].

Consistently, premixing of either [Lig$^2$ZnEt] or [Lig$^3$ZnEt] with benzyl alcohol for 2 hours prior to the addition of rac-LA enabled almost full monomer conversion within 30 minutes.

Table 3 below presents the data obtained for polymerization of rac-lactide in DCM at room temperature, after stirring in Benzyl alcohol for 2 hours.

The poly(lactic acid) (PLA) samples produced by all the catalysts were found to be of substantial isotactic character. It is noteworthy that, in spite of the different degrees of fluxionality and different N-configurations, the zinc complexes of the three ligands were all homochiral-selective and led to PLA's of similar degrees of isotacticity. Lig$^3$Zn-Et exhibited the highest isoselectivity and led to PLA with $P_m$ value as high as 0.80. For the complexes of the chiral Lig$^1$, no appreciable change of tacticity was found between the enantiomerically-pure catalysts (R,R)- and (S,S)-Lig$^1$Zn-Et and the racemic rac-Lig$^1$Zn-Et. This signifies that polymeryl exchange between enantiomers occurs to a limited extent only.

To evaluate the relative contributions of enantiomorphic-site control and chain-end control mechanisms to the isotacticity induction and correlate between catalyst chirality and preferred lactide enantiomer, short polymerization runs aiming at partial conversions with the enantiomerically-pure zinc catalysts of Lig$^1$ were performed. Analysis of the unreacted lactide by chiral-GC showed a low but consistent enantiomeric excess: For (R,R)-Lig$^1$Zn-Et after 84% conversion, the remaining lactide is enriched in the D-enantiomer with enantiomeric excess (e.e.) of 40%, suggesting that this catalyst enantiomer has a slight preference for L-lactide. For the (S,S)-Lig$^1$Zn-Et, after 77% conversion, the remaining lactide was enriched in the L-enantiomer with e.e. of 38%.

These data correspond to a very mild preference for a given lactide enantiomer of k$_{rel}$=1.57-1.70 [see, Keith et. al. Adv. Synth. Catal. 2001, 343, 5-26.] and imply that the main contribution to the isotacticity of the PLA obtained from rac-LA is chain-end control.

Polymerization of Homochiral L-Lactide:

The exemplary catalysts of the present embodiments were found to be active for polymerization of the homochiral L-lactide under the same reaction conditions, yielding PLA of high molecular weight, consistent with the calculated molecular weight and narrow molecular weight distributions. The obtained data is presented in Table 4 below.

TABLE 3

| Entry | Initiator | [I]:[LA]:[BnOH] | Time | Conv. | $M_{n\ (calc)}$ (g/mol$^{-1}$) | $M_n$ (g/mol$^{-1}$) | $M_w/M_n$ | Pm |
|---|---|---|---|---|---|---|---|---|
| 1. | Lig$^2$ZnEt | 1:300:2 | 10 min | 0.75 | 16200 | 14600 | 1.09 | 0.69 |
| 2. | Lig$^2$ZnEt | 1:300:2 | 30 min | 0.95 | 20500 | 22340 | 1.08 | 0.68 |
| 3. | Lig$^3$ZnEt | 1:300:2 | 20 min | 0.63 | 13600 | 11200 | 1.10 | 0.78 |
| 4. | Lig$^3$ZnEt | 1:300:2 | 30 min | 0.90 | 19400 | 13200 | 1.07 | 0.74 |

TABLE 4

| Entry | Initiator | [I]:[LA]:[BnOH] | Time (h) | Conv. | $M_{n\ (calc)}$ (g/mol$^{-1}$) | $M_n$ (g/mol$^{-1}$) | $M_w/M_n$ |
|---|---|---|---|---|---|---|---|
| 1. | Lig$^1$ZnEt | 1:300:1 | 15 min | >0.95 | 43200 | 42800 | 1.09 |
| 2. | Lig$^2$ZnEt | 1:300:1 | 2 h | 0.88 | 38000 | 35400 | 1.1 |

Example 4

Synthesis of Magnesium Complexes

The ligand precursors used for forming zinc ethyl complexes as described in Example 1 were reacted with benzyl magnesium chloride, as shown in Scheme 4 below, and the {ONNN}Mg—Cl complex was obtained as a yellow crystalline solid in high yield. $^1$H-NMR analysis revealed that {ONNN}Mg—Cl had formed as a single rigid stereoisomer, and X-ray diffraction measurements revealed a pentacoordinate mononuclear magnesium complex resembling the corresponding zinc complex.

Scheme 4

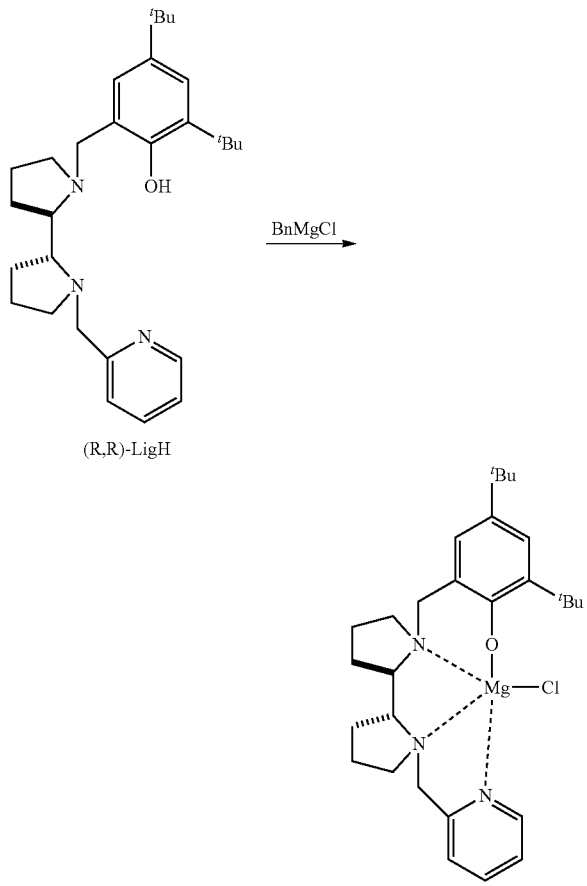

Synthesis of Lig$^1$Mg—Cl

To a stirred solution of (R,R)-Lig$^1$H (110 mg, 0.24 mmol) in toluene (1 mL), was added a solution of BnMgCl (0.24 mL, 1M diethyl ether solution) drop-wise. The resulting mixture was stirred at room temperature for 1 hour until a precipitate appeared. The solvent was removed under vacuum and the residue was washed with pentane to give a yellow solid in 81% yield. The enantiomeric complex (S,S)-Lig$^1$Mg—Cl was prepared accordingly employing (S,S)-Lig$^1$H. X-ray quality crystals of (R,R)-Lig$^1$Mg—Cl were grown from dichloromethane.

$^1$H NMR (CD$_2$Cl$_2$, 500 MHz): δ 8.94 (d, 1H, J=4.91 Hz, ArH), 7.87 (td, 1H, J=1.57 Hz, J=7.73 Hz, ArH), 7.48 (dd, 1H, J=5.21 Hz, 7.66 Hz, ArH), 7.30 (d, 1H, J=7.68 Hz, ArH), 7.18 (d, 1H, J=2.59 Hz, ArH), 6.79 (d, 1H, J=2.65 Hz, ArH), 4.20 (d, 1H, J=14.45 Hz, CH$_2$), 3.84 (d, 1H, J=11.46 Hz, CH$_2$), 3.70 (d, 1H, J=14.52 Hz, CH$_2$), 3.46 (d, 1H, 11.44 Hz, CH$_2$), 3.22-3.16 (m, 2H, CH$_2$), 2.93-2.87 (m, 1H, CH$_2$), 2.80 (qd, 1H, J=2.49 Hz, CH), 2.67 (dt, 1H, J=6.63 Hz, CH$_2$), 2.54-2.50 (m, 1H, CH$_2$), 2.12-2.04 (m, 3H, CH$_2$), 1.96-1.91 (m, 2H, CH$_2$), 1.86-1.84 (m, 1H, CH$_2$), 1.74-1.68 (m, 1H, CH$_2$), 1.59-1.52 (m, 1H, CH$_2$), 1.47 (s, 9H, C(CH$_3$)$_3$), 1.26 (s, 9H, C(CH$_3$)$_3$).

$^{13}$C NMR (CD$_2$Cl$_2$, 125 MHz): δ 163.46 (C), 156.33 (C), 149.34 (CH), 139.60 (CH), 137.20 (C), 134.37 (C), 126.08 (CH), 124.54 (CH), 123.94 (CH), 123.81 (CH), 69.98 (CH$_2$), 67.36 (CH), 63.28 (CH), 59.01 (CH$_2$), 50.91 (CH$_2$), 35.47 (C), 34.06 (C), 32.06 (CH$_3$), 29.78 (CH$_3$), 28.03 (CH$_2$), 26.54 (CH$_2$), 23.95 (CH$_2$), 20.51 (CH$_2$).

HRMS (APPI$^+$): Calc for C$_{29}$H$_{42}$ClMgN$_3$O: 507.2867, found: 507.2874 (M$^+$).

Crystal Data for Complex [(R,R)-LigMg-Cl·CH$_2$Cl$_2$]· C$_{29}$H$_{42}$CiN$_3$OMg, CH$_2$Cl$_2$; M=593.34; orthorhombic; space group P 21 21 21; a=7.9066(5) Å, b=17.5510(13) Å, c=22.4279(18)Å, V=3112.3(4) Å3; T=110(2) K; Z=4; Dc=1.266 g cm-3; μ (Mo Kα)=0.342 mm-1; R1=0.0733 and wR2=0.1718 for 4786 reflections with I>2σ (I); R1=0.0634 and wR2=0.1638 for all 4196 unique reflections.

Synthesis of Lig$^1$Mg-HMDS

To a stirred solution of Mg(HMDS)$_2$ (72 mg, 0.22 mmol) in toluene (1 mL), was added a solution of (R,R)-Lig$^1$H (97 mg, 0.22 mmol) drop-wise. The resulting mixture was stirred at room temperature for 4 hours, and the solvent was removed under vacuum. The residue was washed with pentane to give a white solid in 87% yield. The enantiomeric complex (S,S)-Lig$^1$Mg-HMDS was prepared accordingly employing (S,S)-Lig$^1$H. X-ray quality crystals of (R,R)-Lig$^1$Mg-HMDS were grown from dichloromethane.

$^1$H NMR (C$_6$D$_6$, 500 MHz): δ 9.17 (d, 1H, J=4.95 Hz, ArH), 7.50 (d, 1H, J=2.70 Hz, ArH), 6.90 (d, 1H, J=2.65 Hz, ArH), 6.86 (td, 1H, J=7.68 Hz, J=1.65 Hz, ArH), 6.65 (dd, 1H, J=5.20 Hz, J=7.67 Hz, ArH), 6.18 (d, 1H, J=7.70 Hz, ArH), 4.58 (d, 1H, J=12.15 Hz, CH$_2$), 3.51-3.45 (m, 1H, CH), 3.31 (d, 1H, J=15.30 Hz, CH$_2$), 2.99 (d, 1H, J=12.25 Hz, CH$_2$), 2.96-2.95 (m, 1H, CH), 2.78-2.75 (m, 1H, CH$_2$), 2.73 (d, 1H, J=15.35 Hz, CH$_2$), 2.30-2.25 (m, 2H, CH$_2$), 1.82-1.69 (m, 3H, CH$_2$), 1.57 (s, 9H, C(CH$_3$)$_3$), 1.44 (s, 9H, C(CH$_3$)$_3$), 1.17-1.14 (m, 2H, CH$_2$), 0.97-0.91 (m, 3H, CH$_2$), 0.76 (s, 9H, NC(CH$_3$)$_3$), 0.14 (s, 9H, NC(CH$_3$)$_3$).

Crystal Data for Complex [(R,R)-LigMg-HMDS]· C$_{35}$H$_{60}$N$_4$OMgSi$_2$; M=633.36; orthorhombic; space group P 21 21 21; a=11.4994(6) Å, b=16.5576(7) Å, c=19.7586(8)Å, V=3762.1(3) Å3; T=110(2) K; Z=4; Dc=1.118 g cm-3; μ (Mo Kα)=0.142 mm-1; R1=0.0455 and wR2=0.0833 for 6263 reflections with I>2σ (I); R1=0.0380 and wR2=0.0802 for all 5605 unique reflections.

Molecular representations of the crystallographic structures of Lig$^1$Mg—Cl and Lig$^1$Mg-HMDS are presented in FIGS. 4A and 4B, respectively.

Example 5

Polymerization of lactides using Magnesium Complexes
General Polymerization Procedure (Mg Complexes):

To a solution of the {ONNN}Mg-X catalyst (0.01 mmol, X=Cl or HMDS) in dichloromethane (5 mL), benzyl alcohol (0-0.04 mmol) was added, and the reaction mixture was stirred at room temperature 2 minutes. Then, a lactide (e.g., rac-lactide or L-lactide, 432 mg, 3 mmol) was added, and the reaction was stirred at room temperature. After the desired time, the reaction was terminated by exposing to air and the volatiles were removed under vacuum.

The catalyst was found to exhibit the same activities when employed either in its enantiomerically-pure form or in its racemic form.

The deactivation of the catalyst upon exposure to air was demonstrated by polymerization of 200 equivalents of L-LA under nitrogen atmosphere, exposing the mixture to air for 20 seconds and addition of 100 equivalents of L-LA. The second portion of L-LA had not reacted.

Polymerization in melt was performed by charging a vial with a stir-bar, the catalyst (0.01 mmol), benzyl alcohol (either none or 0.01 mmol) and a lactide (432 mg, 3 mmol). Immersing the vial in an oil bath pre-heated to 130° C. resulted in lactide melting followed by an almost immediate quenching of the stir-bar rotation due to PLA formation. The reaction was terminated by rapid cooling to room temperature and exposing to air.

Table 5 below presents the data obtained for polymerization of rac-lactide in DCM at room temperature.

Table 6 presents the data obtained for polymerization of L-lactide (L-LA) in DCM at room temperature.

Table 7 below presents the data obtained for polymerization of L-lactide (L-LA) in melt.

TABLE 5

| Entry | Initiator | [I]:[BnOH]:[LA] | Time | Conv. | $M_{n(calc)}$ (g/mol$^{-1}$) | $M_n$ (g/mol$^{-1}$) | $M_w/M_n$ | $P_m$ |
|---|---|---|---|---|---|---|---|---|
| 1. | Lig$^1$Mg—Cl | 1:0:300 | 2 min | 0.96 | 41472 | 112420 | 1.37 | 0.89 |
| 2. | Lig$^1$Mg—Cl | 1:1:300 | 2 min | 0.98 | 42336 | 41045 | 1.06 | 0.91 |
| 3. | Lig$^1$Mg—Cl | 1:2:4000 | 2 min | 0.98 | 282240 | 257840 | 1.14 | 0.90 |
| 4. | Lig$^1$Mg-HMDS | 1:0:300 | 3 min | 0.95 | 41040 | 143382 | 1.63 | 0.91 |
| 5. | Lig$^1$Mg-HMDS | 1:1:300 | 3 min | >0.99 | 43200 | 42036 | 1.16 | 0.90 |

TABLE 6

| Initiator | [I]:[BnOH]:[LA] | Time | Conv. | $M_{n\ (calc)}$ (g/mol$^{-1}$) | $M_n$ (g/mol$^{-1}$) | $M_w/M_n$ |
|---|---|---|---|---|---|---|
| Lig$^1$Mg—Cl | 1:1:300 | 1 min | >0.99 | 43200 | 44340 | 1.04 |
| Lig$^1$Mg—Cl | 0.5:1:300 | 1 min | >0.99 | 43200 | 41360 | 1.05 |
| Lig$^1$Mg—Cl | 0.5:2:300 | 1 min | >0.99 | 21600 | 23420 | 1.05 |
| Lig$^1$Mg—Cl | 0.5:1:1000 | 3 min | >0.99 | 144000 | 137560 | 1.06 |
| Lig$^1$Mg—Cl | 0.5:1:2150 | 6 min | >0.99 | 309600 | 266000 | 1.07 |
| Lig$^1$Mg—Cl | 1:0:300 | <20 sec | >0.99 | 43200 | 106600 | 1.28 |
| Lig$^1$Mg—Cl | 1:0:1000 | <40 sec | >0.99 | 144000 | 412400 | 1.35 |

TABLE 7

| Initiator | [I]:[BnOH]:[LA] | Time | Conv. | $M_{n\ (calc)}$ (g/mol$^{-1}$) | $M_n$ (g/mol$^{-1}$) | $M_w/M_n$ |
|---|---|---|---|---|---|---|
| Lig$^1$Mg—Cl | 1:0:300 | <10 sec | 0.42 | 18144 | 28200 | 1.5 |
| Lig$^1$Mg—Cl | 1:1:300 | <10 sec | 0.65 | 28800 | 50200 | 2.3 |

Preliminary runs showed that the addition of 300 equivalents of L-LA to a solution including {ONNN}Mg—Cl and 1 equivalent of benzyl alcohol led to full consumption of the monomer within 1 minute. This corresponds to one of the highest activities ever reported for lactide polymerization.

Gel permeation chromatographic (GPC) analysis of the polymer samples revealed exceptionally narrow molecular weight distributions with typical PDI (polydispersity index: Mw/Mn) values of <1.05, and number-average molecular weights (Mn) that coincided with the monomer/initiator molar ratio. {ONNN}Mg—Cl was found to act as an "immortal polymerization" catalyst as well, namely, it enabled the growth of more than a single polymer chain by every magnesium center by simply employing more than a single equivalent of benzyl alcohol.

The PLA samples obtained under the immortal conditions retained very narrow PDI values, and the measured Mn values were consistent with the calculated values of monomer/benzyl alcohol molar ratio.

The activity of the {ONNN}Mg—Cl complex was examined up to L-LA loading of 4300 equivalents (and 2 equivalents of benzyl alcohol). Full monomer consumption was reached in 6 minutes and the PLLA produced was monodisperse and of very high Mn (see, Table 6).

$^1$H-NMR and HRMS characterization of a mixture of {ONNN}Mg—Cl and benzyl alcohol in dichloromethane revealed that no reaction had taken place. Namely, the ROP catalysis probably follows an activated-monomer mechanism in which the lactide coordinates to the magnesium rather than a coordination-insertion mechanism which would require an {ONNN}Mg-OBn type complex. Consistently, the {ONNN}Mg—Cl complex was found to be highly active even in the absence of alcohol (see Tables 6 and 7).

Example 6

Polymerization of lactone using Magnesium Complexes
General ε-Caprolactone Polymerization Procedure:

To a solution of the {ONNN}Mg-HMDS catalyst (0.01 mmol) in dichloromethane (5 mL), benzyl alcohol (0. –0.5 mmol) was added, and the reaction mixture was stirred at room temperature 2 minutes. Then, ε-caprolactone was added, and the reaction was stirred at room temperature. After the desired time, the reaction was terminated by exposing to air and the volatiles were removed under vacuum.

The obtained data is presented in Table 8

TABLE 8

| [I]:[εCL]:[BnOH] | Time | Conv. | $M_{n\,(calc)}$ (g/mol$^{-1}$) | $M_n$ (g/mol$^{-1}$) | $M_w/M_n$ |
|---|---|---|---|---|---|
| 1:300:0 | 1 min | >0.99 | 34242 | 513264 | 1.33 |
| 1:1000:0 | 1.2 min | >0.99 | 114140 | 485297 | 1.46 |
| 1:300:1 | 2 min | >0.99 | 34242 | 24315 | 1.41 |
| 1:1200:4 | 3 min | >0.99 | 34242 | 29415 | 1.55 |
| 1:3000:10 | 3 min | >0.99 | 34242 | 26297 | 1.48 |
| 1:6000:20 | 3 min | >0.99 | 34242 | 30246 | 1.56 |
| 1:15000:50 | 3 min | >0.99 | 34242 | 28236 | 1.54 |
| 1:4000:4 | 3 min | >0.99 | 114140 | 117990 | 1.63 |

Preliminary runs showed that the addition of 300 equivalents of ε-caprolactone to a solution including {ONNN}Mg-HMDS led to full consumption of the monomer within 1 minute, in the absence of benzyl alcohol, indicating exceptionally high activity for ε-caprolactone polymerization.

Gel permeation chromatographic (GPC) analysis of the polymer samples revealed narrow molecular weight distributions with typical PDI (polydispersity index: Mw/Mn) values, generally within a range of 1.3-1.6, and number-average molecular weights (Mn) that coincided with the monomer/initiator molar ratio.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A process of ring opening polymerization of a cyclic ester, the process comprising contacting the cyclic ester with a catalyst system comprising an organometallic complex represented by Formula I:

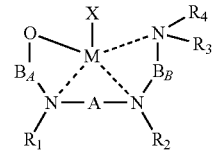

Formula I wherein:
the dashed line represents a coordinative bond;
M is a divalent metal;
X is a monoanionic ligand;
A, $B_A$ and $B_B$ are each independently a bridging moiety of 1 to 12 carbon atoms;
$R_1$ and $R_2$ are each independently hydrogen, alkyl, cycloalkyl, aryl or alternatively, one or both of $R_1$ and $R_2$ form together, optionally with one or more carbon atoms in A, a heteroalicyclic or heteroaromatic, 5-membered, 6-membered or 7-membered ring; and
$R_3$ and $R_4$ are each independently hydrogen, alkyl, cycloalkyl, aryl or alternatively, one or both of $R_3$ and $R_4$ form together with one or more carbon atoms in BB, a heteroalicyclic or heteroaromatic, 5-membered, 6-membered or 7-membered ring, and a co-catalyst.

2. The process of claim 1, wherein M is zinc.
3. The process of claim 2, wherein X is alkyl.
4. The process of claim 1, wherein M is magnesium.
5. The process of claim 4, wherein X is halo or an amine substituted by at least one silyl group.
6. The process of claim 1, wherein said BA bridging moiety has a general Formula:

—(CRaRb)m—C($R_{17}R_{18}$)—C($R_{19}R_{20}$)— wherein:
m is an integer of from 1 to 6, or from 1 to 4, or from 1 to 2;
Ra and Rb are each independently hydrogen, alkyl, cycloalkyl, aryl, heteroaryl, heteroalicyclic, hydroxyl, alkoxy, thiol, thioalkoxy, aryloxy, and amine, wherein when m is other than 1, Ra and Rb in each (CRaRb) unit can be the same or different, and one or both Ra and Rb in one unit can form a 5-membered, 6-membered or 7-membered alicyclic, heteroalicyclic, aromatic or heteroaromatic ring with one or both Ra and Rb of an adjacent unit; and
$R_{17}$-$R_{20}$ are each independently hydrogen, alkyl, cycloalkyl, aryl, heteroaryl, heteroalicyclic, hydroxyl, alkoxy, thiol, thioalkoxy, aryloxy, and amine, or, alternatively, two or more of $R_{17}$-$R_{20}$ form together a 5-membered, 6-membered or 7-membered alicyclic, heteroalicyclic, aromatic or heteroaromatic ring.

7. The process of claim 6, wherein:
m is 1; and/or
Ra and Rb are each hydrogen; and/or
$R_{17}$-$R_{20}$ form together a substituted or unsubstituted aromatic ring.

8. The process of claim 1, wherein said BB bridging moiety has a general Formula:

—(CRcRd)$n$-C($R_{21}R_{22}$)— wherein:
n is an integer of from 1 to 6, or from 1 to 4, or from 1 to 2;
Rc and Rd are each independently hydrogen, alkyl, cycloalkyl, aryl, heteroaryl, heteroalicyclic, hydroxyl, alkoxy, thiol, thioalkoxy, aryloxy, and amine, wherein when n is other than 1, Rc and Rd in each (CRcRd) unit can be the same or different, and one or both Rc and Rd in one unit can form a 5-membered, 6-membered or 7-membered alicyclic, heteroalicyclic, aromatic or heteroaromatic ring with one or both Rc and Rd of an adjacent unit; and
$R_{21}$ and $R_{22}$ are each independently hydrogen, alkyl, cycloalkyl, aryl, heteroaryl, heteroalicyclic, hydroxyl, alkoxy, thiol, thioalkoxy, aryloxy, and amine, or, alternatively, at least two of $R_3$, $R_4$, $R_{21}$ and $R_{22}$ form together a 5-membered, 6-membered or 7-membered heteroalicyclic or heteroaromatic ring.

9. The process of claim 8, wherein:
n is 1; and/or
Rc and Rd are each hydrogen; and/or
$R_3$, $R_4$, $R_{21}$ and $R_{22}$ form together a substituted or unsubstituted heteroaromatic ring.

10. The process of claim 8, wherein said complex is represented by Formula IA:

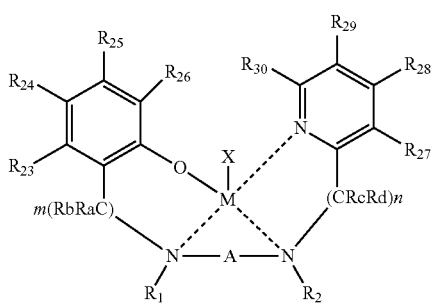

Formula IA wherein:
$R_{23}$-$R_{30}$ are each independently selected from the group consisting of hydrogen, alkyl, cycloalkyl, aryl, halo, alkoxy, aryloxy, trialkylsilyl, heteroalicyclic, heteroaryl and amine.

11. The process of claim 10, wherein:
at least one of $R_{23}$-$R_{26}$ is alkyl; and/or
at least one of $R_{24}$ and $R_{26}$ is alkyl; and/or
at least one of $R_{23}$-$R_{26}$ is halo; and/or
at least one of $R_{23}$-$R_{26}$ is a bulky rigid group.

12. The process of claim 10, wherein each of $R_{27}$-$R_{30}$ is hydrogen.

13. The process of claim 10, wherein at least one of $R_{27}$-$R_{30}$ is a heteroalicyclic or a heteroaryl.

14. The process of claim 1, wherein said A bridging moiety has a general Formula A1, A2 or A3:

 Formula A1

 Formula A2

 Formula A3 wherein $R_5$-$R_{12}$, $R_{15}$ and $R_{16}$ are each independently selected from the group consisting of hydrogen, alkyl, cycloalkyl, aryl, heteroaryl and heteroalicyclic, $R_{13}$ and $R_{14}$ are each independently selected from the group consisting of hydrogen, alkyl, cycloalkyl, aryl, heteroaryl, heteroalicyclic, hydroxyl, alkoxy, thiol, thioalkoxy, aryloxy, and amine or, alternatively, at least two of $R_1$, $R_2$ and $R_5$-$R_6$ in Formula A1, or at least two of $R_1$, $R_2$ and $R_7$-$R_{10}$ in Formula A2 or at least two of $R_1$, $R_2$ and $R_{11}$-$R_{16}$ in Formula A3 form a 5 to 7-membered alicyclic, heteroalicyclic, aromatic or heterocyclic ring.

15. The process of claim 14, wherein said bridging moiety has said Formula A2.

16. The process of claim 15, wherein:
each of $R_7$-$R_{10}$ is hydrogen; or
$R_7$ and $R_1$ form said heteroalicyclic ring; or
$R_9$ and $R_2$ form said heteroalicyclic ring; or
at least one, or both, of $R_1$ and $R_2$ is alkyl.

17. The process of claim 1, wherein said co-catalyst is Rk-OH, wherein Rk is alkyl, cycloalkyl, alkaryl or aryl.

18. The process of claim 1, wherein said cyclic ester is a lactide.

19. The process of claim 1, wherein said cyclic ester is a lactone.

* * * * *